United States Patent [19]

Molnar et al.

[11] Patent Number: 5,143,680
[45] Date of Patent: Sep. 1, 1992

[54] METHOD AND APPARATUS FOR DEPOSITING MOISTURE-ABSORBENT AND THERMOPLASTIC MATERIAL IN A SUBSTRATE

[75] Inventors: Julius J. Molnar, Amherst; Ernest J. Fena, Rocky River, both of Ohio; David W. Folden, Delmont, Pa.; Douglas A. Schneider; Richard A. Becker, both of Lorain, Ohio; Charles L. Fimmen, Elyria, Ohio; David M. Selestak, Avon, Ohio; Robert Shlapak, Wakeman, Ohio

[73] Assignee: Nordson Corporation, Westlake, Ohio

[21] Appl. No.: 525,880
[22] Filed: May 17, 1990
[51] Int. Cl.$^5$ .............................................. D04H 1/70
[52] U.S. Cl. ...................................... 264/511; 264/518; 264/113; 425/81.1; 425/83.1
[58] Field of Search ............... 264/518, 113, 510, 511, 264/6, 12; 425/80.1, 81.1, 82.1, 83.1

[56] References Cited

U.S. PATENT DOCUMENTS

| | | | |
|---|---|---|---|
| 2,357,392 | 9/1944 | Francis, Jr. ........................... | 26/264 |
| 2,466,906 | 4/1949 | Miller .................................... | 264/24 |
| 2,707,690 | 5/1955 | Pearson ................................. | 65/3.43 |
| 3,381,069 | 4/1968 | Simison ................................. | 264/518 |
| 3,669,103 | 6/1972 | Harper et al. ........................ | 128/156 |
| 3,670,731 | 6/1972 | Harmon ................................ | 604/368 |
| 3,715,251 | 2/1973 | Prentice ................................ | 156/62.8 |
| 3,939,532 | 2/1976 | Wiegand ............................... | 264/518 |
| 3,967,623 | 7/1976 | Butterworth et al. | |
| 3,984,272 | 10/1976 | Teed ..................................... | 156/201 |
| 4,045,833 | 9/1977 | Mesek et al. ......................... | 5/484 |
| 4,118,531 | 10/1978 | Hauser ................................. | 428/224 |
| 4,123,211 | 10/1978 | Rudloff ................................ | 425/82.1 |
| 4,186,165 | 1/1980 | Aberson et al. ..................... | 424/484 |
| 4,319,870 | 3/1982 | Slama ................................... | 425/83.1 |
| 4,333,463 | 6/1982 | Holtman .............................. | 604/368 |
| 4,351,660 | 9/1982 | Plantard et al. ...................... | 65/5 |
| 4,364,992 | 12/1982 | Ito et al. ............................... | 428/283 |
| 4,381,783 | 5/1983 | Elias .................................... | 604/368 |
| 4,415,388 | 11/1983 | Korpman ............................. | 156/78 |
| 4,429,001 | 1/1984 | Kolpin et al. ........................ | 428/283 |
| 4,469,734 | 9/1984 | Minto et al. ......................... | 428/134 |
| 4,480,947 | 11/1984 | Nagasaka ............................. | 406/14 |
| 4,551,191 | 11/1985 | Kock et al. .......................... | 156/276 |
| 4,559,050 | 12/1985 | Iskra .................................... | 604/368 |
| 4,610,678 | 9/1986 | Weisman et al. .................... | 604/368 |
| 4,640,810 | 2/1987 | Laursen et al. ...................... | 264/518 |
| 4,666,647 | 5/1987 | Enloe et al. ......................... | 261/121 |
| 4,675,209 | 6/1987 | Pedigrew ............................. | 427/194 |
| 4,724,114 | 2/1988 | McFarland et al. ................. | 264/510 |
| 4,773,903 | 9/1988 | Weisman et al. .................... | 604/368 |
| 4,894,277 | 1/1990 | Akasaki ............................... | 428/198 |
| 4,904,440 | 2/1990 | Angstadt ............................. | 264/517 |
| 4,908,175 | 3/1990 | Angstadt ............................. | 264/113 |
| 4,927,346 | 5/1990 | Kaiser et al. ........................ | 425/81.1 |
| 4,927,582 | 5/1990 | Bryson ................................ | 264/113 |

FOREIGN PATENT DOCUMENTS

| | | |
|---|---|---|
| 0007149 | 1/1980 | European Pat. Off. . |
| 0053928 | 6/1982 | European Pat. Off. . |
| 0085729 | 11/1985 | European Pat. Off. . |
| 0174775 | 3/1986 | European Pat. Off. . |
| 0198683 | 10/1986 | European Pat. Off. . |
| 1510427 | 10/1970 | Fed. Rep. of Germany . |
| G8209936.7 | 3/1982 | Fed. Rep. of Germany . |
| 2150033 | 6/1985 | United Kingdom . |

Primary Examiner—Mary Lynn Theisen
Attorney, Agent, or Firm—Wood, Herron & Evans

[57] ABSTRACT

A method and apparatus for forming a non-woven pad of fibrous material is provided in which highly moisture-absorbent particles and fibers of thermoplastic material are intermixed with the fibrous material throughout one or more predetermined portions of the thickness of the non-woven pad while maintaining other portions of the thickness of the pad substantially free of highly moisture-absorbent particles and/or thermoplastic fiber material. The non-woven pad is formed on one side of a conveyor moving through a forming chamber which has a duct connected to a source of vacuum operable to draw fibrous material injected into the chamber onto the conveyor. One dispenser discharges the highly moisture-absorbent material at a predetermined location relative to the fibrous material being drawn onto the conveyor, and at least one other dispenser discharges the thermoplastic fiber material into the chamber at a location to intermix the thermoplastic fiber material with the fibrous material and highly moisture-absorbent material being drawn onto the conveyor at the predetermined location, and/or to intermix the thermoplastic fiber materials with the fibrous material in areas of the thickness of the non-woven pad on one or both sides of the highly moisture-absorbent material.

78 Claims, 6 Drawing Sheets

METHOD AND APPARATUS FOR DEPOSITING MOISTURE-ABSORBENT AND THERMOPLASTIC MATERIAL IN A SUBSTRATE

FIELD OF THE INVENTION

This invention relates to a method and apparatus for making moisture-absorbent substrates, and, more particularly, to a method and apparatus for interspersing highly moisture-absorbent particles and thermoplastic hot melt adhesive material throughout predetermined portions of a fibrous material pad in a non-woven product.

BACKGROUND OF THE INVENTION

Hygienic articles such as disposable diapers, sanitary napkins, incontinence pads and sick bed sheets must have a high moisture absorption capacity to effectively retain eliminated body fluids for acceptable periods of time. Early hygienic articles of this type employed cellulose wadding, fluff cellulose or absorbent cotton as the absorbent materials. One problem with these materials is that their moisture-retaining capacity is relatively small compared to their volume. In order to improve the moisture-retaining capacity of hygienic articles made from these materials, the volume of such absorbent materials in the hygienic article must be increased. This produces a bulky product which is unacceptable in many hygienic articles, particularly sanitary napkins.

In an effort to reduce the volume and size of hygienic articles, and increase their absorbent capacity, one layer of such articles comprises a non-woven pad formed of cellulose fluff, wood pulp, textile fibers or other non-woven fibrous materials in which highly moisture-absorbent material is combined within the fiber structure of the pad. These highly moisture-absorbent materials are preferably water-insoluble absorbent polymers having a high capacity for absorbing water and body fluids, which are partially or wholly synthetic and are commercially available in fine-grain, particulate form. See, for example, U.S. Pat. Nos. 3,997,484; 3,661,815; 4,117,222; and, 3,936,441.

One system for forming the non-woven fibrous materials into a non-woven pad is disclosed in U.S. Pat. No. 3,984,272 In this system, a forming chamber having an inlet and outlet is connected by a feed conduit to a source of fibrous materials such as finely ground wood pulp. A perforated conveyor is movable through the forming chamber between its inlet and outlet, and structure is provided to draw a vacuum on one side of the perforated conveyor. The fibrous material introduced into the chamber is drawn onto the opposite side of the conveyor by the vacuum, and this fibrous material forms a non-woven pad on the conveyor which increases in thickness in a direction from the inlet of the chamber toward its outlet. The non-woven pad thus has a bottom surface resting atop the conveyor and a top surface which angles or slopes upwardly relative to the conveyor from the inlet of the chamber toward its outlet. A leveling or scarfing roller near the outlet of the forming chamber is operative to remove at least a portion of the fibrous material at the top of the non-woven pad to produce a non-woven pad of uniform thickness. The pad is then transmitted by the conveyor through the outlet of the forming chamber for subsequent operations to form the completed hygienic article.

Two methods have been employed to incorporate highly moisture-absorbent material into the non-woven pad formed within the forming chamber in systems of the type disclosed in U.S. Pat. No. 3,984,272 and described above. In one method, the highly moisture-absorbent material is injected into the same feed conduit which supplies the fibrous material into the interior of the chamber. The highly moisture-absorbent material and fibrous material are intermixed within the feed conduit to completely intersperse the moisture-absorbent material throughout the fibers prior to introduction into the forming chamber. This produces a non-woven pad atop the conveyor within the chamber in which the moisture-absorbent material is present throughout the entire thickness, width and length of the non-woven pad.

One problem with the above-described method is the loss of moisture-absorbent material through the perforated conveyor in the forming chamber. As the fibers and moisture-absorbent material mixture is drawn onto the perforated conveyor to form the non-woven pad, moisture-absorbent material at the lower portion of the non-woven pad is drawn through the conveyor into a filter-reclamation system. Some of the moisture-absorbent material is lost. Additionally, the moisture-absorbent material is difficult to contain even with the filtering system, and environmental contamination can result.

Another problem with this method is that the moisture-absorbent material is distributed throughout the non-woven pad across its entire length, width and thickness. This produces substantial waste because in subsequent forming operations, the non-woven pad is cut to the desired length of the hygienic article. In addition, the application of moisture-absorbent material across the entire width of the non-woven pad may be unnecessary for some types of hygienic articles, particularly disposable diapers where the leg holes are cut at the edges of the layer.

Another method of combining moisture-absorbent material with the non-woven pads employed in hygienic articles involves the application of moisture-absorbent material onto the top surface of the non-woven pad downstream from the leveling or scarfing rollers and outside of the forming chamber. Accordingly, a non-woven pad is produced having moisture-absorbent material concentrated on its top surface with substantially no moisture-absorbent material within the remaining thickness of the pad.

One disadvantage of this second method relates to the handling and loss of the moisture-absorbent material applied to the pad. Because the application of moisture-absorbent material takes place outside of the forming chamber in this method, a relatively expensive collection system is required to capture the oversprayed moisture-absorbent material and prevent it from escaping to the environment. Migration of the moisture-absorbent material out of the pad is a particular problem in this method because all of the powder is concentrated at its top surface. In particulate or granular form, the moisture-absorbent material can be readily dislodged from the type of pads which are not sealed at the ends.

Another problem with this second method of incorporating the highly moisture-absorbent material into the non-woven pad is that the material is concentrated on top of the pad. This causes so-called "gel blockage" wherein the moisture-absorbent material at the top of the non-woven pad become saturated with fluid and prevents the wicking or transfer of moisture to the fibrous material in the remaining portion of the pad. As a result, the fluid is retained at the surface of the pad in contact with the wearer of the hygienic article causing discomfort. Additionally, only a relatively small portion of the entire thickness of the pad is effectively employed to absorb the moisture.

These problems have been addressed in U.S. patent application Ser. No. 07/348,149, filed May 2, 1989, and entitled "Apparatus For Depositing Moisture-Absorbent Material In A Substrate", which is commonly owned by the assignee of the instant application. The apparatus disclosed in patent application Ser. No. 07/348,149 employs essentially the same type of forming chamber disclosed in U.S. Pat. No. 3,984,272, but is effective to intermix highly moisture-absorbent material with fibrous material in a predetermined portion of the thickness of the pad and, if desired, at longitudinally spaced locations therealong. A dispenser, such as a spray gun, is located at least partially within the forming chamber at a predetermined location with respect to the upwardly sloping top surface of the non-woven pad of fibrous material being drawn onto the conveyor. The dispenser is effective to intermix highly moisture-absorbent material with a portion of the fibrous material being drawn onto the conveyor at such predetermined location. This forms a layer of intermixed fibrous material and particulate material within a predetermined portion of the thickness of the pad while maintaining another portion of the thickness of the non-woven pad substantially free of particulate material.

Expressed in other terms, the apparatus disclosed in Ser. No. 07/348,149 forms a non-woven pad in which fibrous material is drawn onto the conveyor beginning at the inlet to the forming chamber, and such fibrous material begins to build up on the conveyor between the inlet and the location of the spray gun for the highly moisture-absorbent material. This forms a bottom layer of the non-woven pad resting directly on the conveyor which increases in thickness in the direction of movement of the conveyor through the chamber. The spray gun intermixes a second material, e.g., highly moisture-absorbent particulate material, with the fibrous material being drawn onto the conveyor at the predetermined location where the spray gun is positioned at least partially within the forming chamber. This intermixture of fibrous material and particulate material forms an intermediate layer which is drawn onto the bottom layer of fibrous material already accumulated on the conveyor upstream from the location of the spray gun. As the conveyor continues moving toward the outlet of the forming chamber, additional fibrous material is drawn toward the conveyor forming a top layer of fibrous material over the intermediate layer of intermixed fibrous material and moisture-absorbent material. As a result, a non-woven pad is formed having a bottom layer of fibrous material, an intermediate layer of intermixed fibrous material and particulate material and a top layer of fibrous material wherein the top and bottom layers of fibrous material are substantially free of moisture-absorbent material.

The apparatus described above which is the subject of Ser. No. 07/348,149 substantially improves upon the methods described above in a number of respects. The problem of gel blockage is substantially eliminated because the highly absorbent material is concentrated preferably at the core or center portion of the non-woven pad as opposed to near its upper surface. The loss of the particulate moisture-absorbent material is reduced and problems of overspray of such material are substantially eliminated. Additionally, by locating the moisture-absorbent material at selected areas within the thickness and length of the pad, a substantial savings in the amount of moisture-absorbent material required is achieved.

Despite the improvements obtained by the apparatus disclosed in Ser. No. 07/348,149, certain limitations have been observed in the manufacture of non-woven pads for some types of hygienic articles. For example, even though the highly moisture-absorbent, particulate material is concentrated within the center layer of the non-woven core using such method and apparatus, migration of the particulate material through the surrounding fibrous material layers can still occur. Given the further steps required in the process for forming the completed hygienic article, and the packaging and shipment of such hygienic articles, migration of the highly absorbent particulate material into the surrounding fibrous material or entirely through the non-woven pad is a possibility.

Additionally, it is desirable to increase the structural integrity of the non-woven pad, and particularly that portion of the thickness of the pad containing the highly moisture-absorbent material. It has been found that when the non-woven pad becomes wet, with such wetness being concentrated in the area of the highly moisture-absorbent material, the integrity and stability of the center of the pad is reduced and can present problems of tearing.

SUMMARY OF THE INVENTION

It is therefore among the objectives of this invention to provide a method and apparatus for the formation of a pad of non-woven fibrous material containing a second material such as moisture-absorbent material interspersed throughout a predetermined portion of the thickness of the non-woven pad, which minimizes waste of the moisture-absorbent material, which increases the structural integrity and stability of the non-woven pad and which permits the use of less fibrous material while maintaining the moisture-retaining capacity of the non-woven pad.

These objectives are accomplished in a method and apparatus of forming a non-woven pad of fibrous material in which fibers such as cellulose fluff, wood pulp, textile fibers or similar materials are introduced through a feed conduit into a forming chamber having an inlet and an outlet. A perforated conveyor is movable between the inlet and outlet of the forming chamber and a vacuum is applied on one side of the conveyor to draw the fibrous material onto the opposite side of the conveyor. In the course of being drawn onto the perforated conveyor, the fibrous material forms a non-woven pad having a bottom surface resting atop the conveyor and a top surface which slopes upwardly relative to the conveyor from the inlet of the chamber toward its outlet. At a predetermined location relative to the sloped, top surface of the non-woven pad, a dispenser located at least partially within the chamber is effective to intermix highly moisture-absorbent material with the fibrous material being drawn onto the conveyor at such predetermined location. Simultaneously, a second dispenser, also disposed at least partially within the interior of the chamber, is effective to intermix a thermoplastic hot melt adhesive in strand or fiber form, or other polymeric binder material, with the fibrous material and moisture-absorbent material being drawn onto the conveyor at such predetermined location. As a result, a layer of intermixed fibrous material, moisture-absorbent material and thermoplastic fibers is formed within a predetermined portion of the thickness of the non-woven pad while maintaining another portion of the thickness of the non-woven pad substantially free of the moisture-absorbent material and thermoplastic fibers.

This invention is therefore predicated upon the concept, in one presently preferred embodiment, of forming a non-woven pad having a discreet layer of intermixed fibrous material, moisture-absorbent material and thermoplastic fibers within a predetermined portion of the thickness of the pad while the remainder of the pad is maintained substantially free of the moisture-absorbent material and thermoplastic fibers. One purpose of the thermoplastic fibers in this embodiment is to become entangled with the fibrous material and moisture-absorbent material to help retain the moisture-absorbent material in position within such layer of the non-woven pad. Preferably, the moisture-absorbent material is located at the center portion or layer of the pad, and the thermoplastic fibers are effective to substantially retain the moisture-absorbent material in such location and prevent its migration to the adjacent top and bottom layers of the non-woven pad. This reduces loss of the moisture-absorbent material, and thus enhances the moisture-absorbent capacity of such non-woven pad.

In another aspect of this embodiment, the thermoplastic fibers intermixed with the fibrous material and moisture-absorbent material at the center of the non-woven pad also function to enhance the stability and structural integrity of such layer. Particularly when the pad becomes wet, the center portion of the pad containing the moisture-absorbent material becomes heavy and concentrated with fluid because of the presence of the moisture-absorbent material and its capacity for absorbing a substantial volume of fluid. The thermoplastic fibers intermixed within this center layer of the non-woven pad helps stabilize such layer and increase its resistance to tearing, particularly when wet. It is contemplated that certain types of polymeric binder materials, such as polyamides, are particularly useful and effective to increase the tear strength and stability of such center layer of the non-woven pad formed in accordance with the method and apparatus of this invention.

In another aspect of this invention, the amount of fibrous material used to form the pad can be reduced in that the invention permits the use of a greater amount of moisture-absorbent material. This is because the thermoplastic fiber material supplied into the pad more effectively retains the moisture-absorbent material within the center portion of the pad where the moisture-absorbent material is typically originally applied. Thus, more moisture-absorbent material can be retained in the center portion of the pad without the problem of a significant portion of the moisture absorbent material drifting from the center of the pad to the bottom of the pad where it would be less effective in increasing the moisture-absorbent capacity of the pad.

In another aspect of this invention, a liquid surfactant can be applied with the thermoplastic fiber material to enhance the wicking capability of the thermoplastic fibers to improve the moisture-absorbent capacity of the pad. This surfactant can be intermixed with the thermoplastic material in the thermoplastic material supply container, can be mixed in with the heated air supplied to the thermoplastic material die head, or can be sprayed into the forming chamber through a spray gun positioned adjacent to the thermoplastic material die head.

In an alternative embodiment of this invention, two separate dispensers for thermoplastic fibers are at least partially disposed within the interior of the forming chamber to intermix two types of thermoplastic polymeric binder materials with the fibrous material and highly moisture-absorbent material being drawn onto a predetermined location relative to the conveyor and the non-woven pad formed thereon. This produces a layer within the interior of the non-woven pad comprising intermixed fibrous material, moisture-absorbent material and the two types of thermoplastic materials. One of these thermoplastic materials is preferably a polyamide, or another suitable type of thermoplastic polymeric binder material having relatively high tensile strength, so that the integrity and stability of the center, intermixed layer of the non-woven pad is enhanced. The other thermoplastic polymeric binder material intermixed within this center layer is preferably a polyethylene, or an equivalent, which helps maintain air gaps or spaces between the fibrous material in such layer. In this manner, the "loft" or thickness of the fluff or fibrous material forming such center layer is retained to enhance the softness and fluff-like feel of the overall non-woven pad.

In another embodiment of this invention, two thermoplastic fiber material dispensers are employed to introduce thermoplastic fibers on either side of the predetermined location where the highly moisture-absorbent material is intermixed with fibrous material. One thermoplastic fiber material dispenser is positioned to intermix thermoplastic fibers with fibrous material being drawn onto the conveyor upstream from the predetermined location, and the other thermoplastic fiber material dispenser is positioned to intermix thermoplastic fibers with the fibrous material being drawn onto the conveyor downstream from such predetermined location. This produces a non-woven pad which is formed with three discreet layers within the thickness thereof including a center layer of intermixed fibrous material and moisture-absorbent material, and top and bottom layers of intermixed fibrous material and thermoplastic fibers on either side of the center layer. The purpose of these top and bottom layers of intermixed fibrous material and thermoplastic fibers is to form barriers on either side of the center layer to reduce or eliminate migration of the moisture-absorbent material outwardly from the interior of the pad.

In the presently preferred embodiment, each of the dispensers employed to introduce thermoplastic polymeric binder material into the interior of the forming chamber are extrusion die heads which are effective to form relatively thin strands or fibers of polymeric binder material, such as hot melt adhesive, and direct such thermoplastic fibers into the forming chamber. The thermoplastic fiber producing die head herein comprises a die head body formed with an inlet which transmits hot melt adhesive material to a number of adhesive passageways. The die head body also includes an air cap connected to a source of heated air which transmits heated air into a number of air passageways formed in the die head body. A nozzle block is attached to the die head body which is formed with a central, adhesive discharge plenum having a plurality of discharge outlets, and a pair of air discharge plenums formed on either side of the adhesive discharge plenum.

Hot melt adhesive is introduced through the inlet and adhesive passageways of the die head body into the adhesive discharge plenum in the nozzle block where it is ejected from the discharge outlets therein as a number of individual adhesive strands or extrusions. At the same time, heated air is transmitted from the air cap and air passageways in the die head body into the air discharge plenums on either side of the nozzle block. The heated air is discharged from elongated outlets in the air discharge plenums, at an angle with respect to the adhesive strands, such that the heated air impacts the adhesive strands and forms elongated, thermoplastic fibers. These thermoplastic fibers are propelled by the force of the heated air into the forming chamber and toward the conveyor for intermixture with the fibrous material and/or moisture-absorbent material, as described above.

DESCRIPTION OF THE DRAWINGS

The structure, operation and advantages of the presently preferred embodiment of this invention will become further apparent upon consideration of the following description, taken in conjunction with the accompanying drawings, wherein.

DETAILED DESCRIPTION OF THE INVENTION

Figure 1:
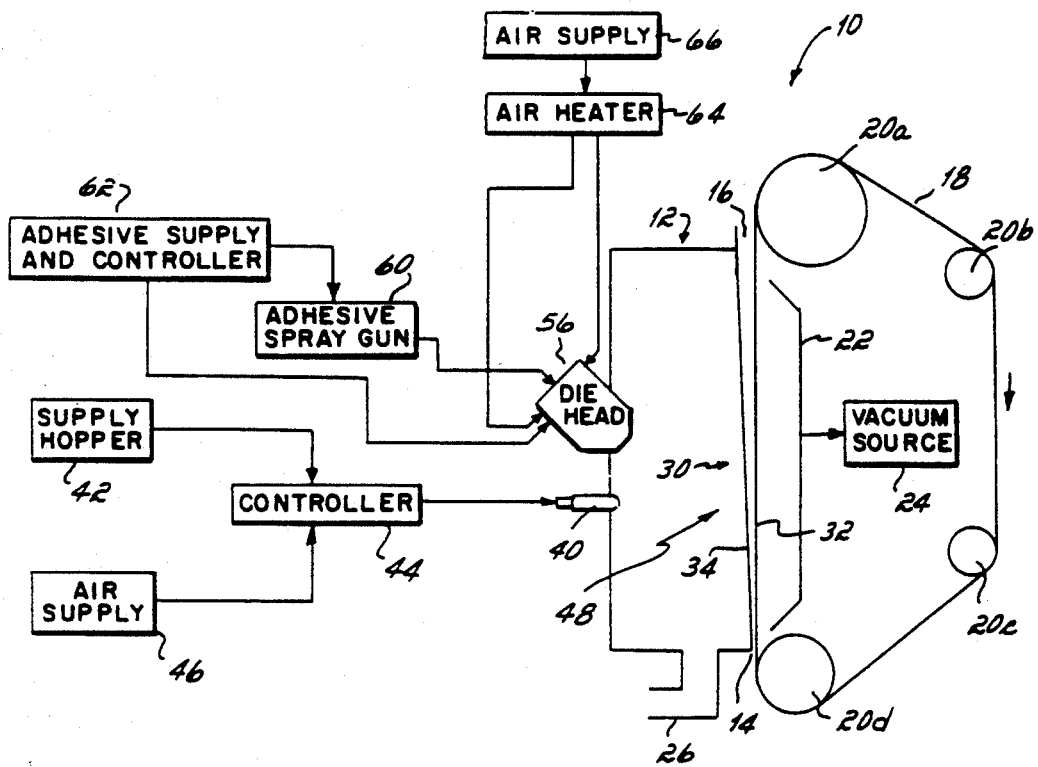
FIG. 1 is a schematic, elevational view of one embodiment of the method and apparatus of this invention.
Figure 2:
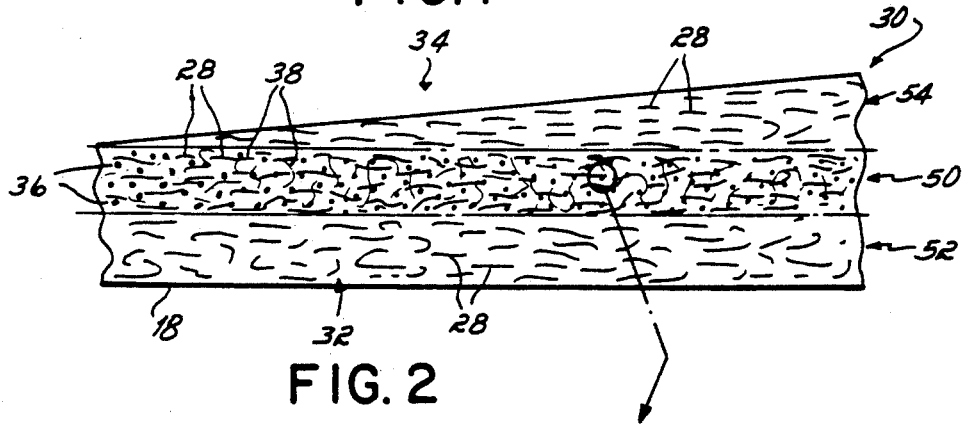
FIG. 2 is an enlarged, partial view of the non-woven pad formed by the apparatus of FIG. 1.

Referring now to FIGS. 1 and 2, an apparatus 10 is illustrated for forming a pad of non-woven, fibrous material having moisture-absorbent material and thermoplastic fibers interspersed throughout selected portions of the pad as described below. The apparatus 10 comprises a forming chamber 12 having an inlet 14 and an outlet 16. An endless perforated conveyor 18 carried by feed rollers 20a–d is movable through the forming chamber 12 between its inlet 14 and outlet 16 in the direction indicated by the arrows in FIG. 1. The conveyor 18 is movable over a plenum 22 mounted on one side of the perforated conveyor 18, and this plenum 22 is connected to a vacuum source 24.

A fiber supply conduit 26 is connected to the conveyor inlet end of forming chamber 12 at a position near the bottom of forming chamber 12 as viewed in FIG. 1. The fiber supply conduit 26 is connected to a source (not shown) of fibrous material 28 such as cellulose fluff, wood pulp, textile fibers or other suitable fibrous materials. The fibrous material 28 is pulled into the forming chamber 12 and drawn onto the conveyor 18 by operation of the vacuum source 24 and plenum 22. As illustrated in FIGS. 1 and 2, the vacuum applied on one side of the conveyor 18 through the plenum 22 is effective to cause the fibrous material 28 to be drawn onto the opposite side of conveyor 18 between the inlet 14 of forming chamber 12, where the plenum 22 begins, and the outlet 16 of forming chamber 12 where the plenum 22 ends. As the conveyor 18 moves through the forming chamber 12, progressively more fibrous material 28 is drawn onto the conveyor 18 forming a non-woven pad 30 of intertwined wood pulp or fluff fibers whose thickness gradually increases from an area of minimum thickness near the inlet 14 of forming chamber 12 to an area of maximum thickness at the outlet 16 thereof. The non-woven pad 30 thus has a bottom surface 32 resting on one side of the conveyor 18, and a top surface 34 which slopes upwardly relative to the conveyor 18 from the inlet 14 toward the outlet 16 of forming chamber 12.

A principal feature of this invention is the formation of a non-woven pad 30 in which highly moisture-absorbent material and thermoplastic, polymeric binder material are intermixed with selected portions of the fibrous material 28 being drawn onto the conveyor 18 such that the moisture-absorbent material and thermoplastic material are interspersed throughout selected portions of the thickness of the non-woven pad 30. The moisture-absorbent material employed in the method and apparatus of this invention is preferably a substantially water-insoluble absorbent polymer having a high capacity for absorbing water and body fluids, as disclosed, for example, in U.S. Pat. Nos. 3,997,484; 3,661,815; 4,117,222; and, 3,936,441, the disclosures of which are incorporated by reference in their entireties herein. As viewed in the Figures, the moisture-absorbent material is depicted in the form of granules or particles 36, but it is contemplated that such moisture-absorbent material could take other forms such as strands or the like. Additionally, the polymeric binder material discussed herein is intended to refer to thermoplastic materials such as hot melt adhesive material, preferably in the form of thermoplastic fibers 38, i.e., thin, strand-like strings or fibers of hot melt adhesive made with a die head of the type described below. It is contemplated, however, that such polymeric binder material could be introduced into the chamber 12 other than in fiber form, as desired.

A method and apparatus for introducing moisture-absorbent particles 36 into a predetermined portion of the non-woven pad 30, while maintaining other portions of the non-woven pad 30 free of such particles 36, is disclosed in U.S. patent application Ser. No. 07/348,149, filed May 2, 1989, and entitled "Apparatus For Depositing Moisture-Absorbent Material In A Substrate", which is commonly assigned to the assignee of this invention, and the disclosure of which is incorporated by reference in its entirety herein. As discussed in detail in Ser. No. 07/348,149, the moisture-absorbent particles 36 are introduced into the non-woven pad 30 by a spray gun 40 of the type disclosed in U.S. Pat. No. 4,600,603, assigned to the same assignee as this invention, the disclosure of which is incorporated by reference in its entirety herein. Particles 36 are supplied to spray gun 40 from a supply hopper 42 connected to an electrical controller 44, such as a programmable controller, which is also connected to an air supply 46. The spray gun 40 is operative to discharge the moisture-absorbent particles 36 into the interior of forming chamber 12 at a predetermined location 48 along the angled, top surface 34 of the non-woven pad 30 being formed on the conveyor 18. Depending on the position of the spray gun 40 and the velocity at which the moisture-absorbent particles 36 are discharged therefrom, as discussed in detail in U.S. Ser. No. 07/348,149, the moisture-absorbent particles 36 intermix with the fibrous material 28 being drawn onto the conveyor 18 at the predetermined location 48 to form a center layer 50 of intermixed fibrous material 28 and moisture-absorbent particles 36 within a predetermined portion of the thickness of non-woven pad 30 while maintaining the other portions of the non-woven pad 30 substantially free of moisture-absorbent particles 36. See FIG. 2.

As viewed in FIGS. 1 and 2, the separate, center layer 50 within the thickness of non-woven pad 30 is obtained, in part, by the discharge of moisture-absorbent particles 36 at the predetermined location 48. The fibrous material 28 introduced into the forming chamber 12 is drawn onto the conveyor 18 and begins to build up as the conveyor 18 moves through the forming chamber 12. By the time the conveyor 18 reaches the predetermined location 48 where the spray gun 40 is positioned, a bottom section or layer 52 of the non-woven pad 30 has already been formed. The moisture-absorbent particles 36 discharged from the spray gun 40 intermix with the fibrous material 28 in the vicinity of the predetermined location 48, and this mixture is drawn toward the conveyor 18 atop the bottom layer 52 of the non-woven pad 30 which has already been formed. Accordingly, the center layer 50 of intermixed moisture-absorbent particles 36 and fibrous material 28 is formed atop the bottom layer 52. The conveyor 18 then continues to move toward the outlet 16 of forming chamber 12, downstream from the predetermined location 48 and spray gun 40, where additional fibrous material 28 is drawn toward the conveyor and atop the center layer 50 to form a top section or layer 54 of the non-woven pad 30. As viewed in FIG. 2, a non-woven pad 30 is thus formed having a bottom layer 52 of fibrous material 28, and intermediate or center layer 50 of intermixed moisture-absorbent particles 36 and fibrous material 28, and a top layer 54 of fibrous material 28 wherein the bottom and top layers 52, 54 are substantially free of moisture-absorbent particles 36.

Figure 2A:
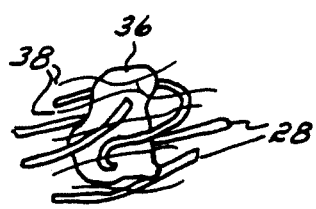
FIG. 2A is an enlarged, schematic view of the circled area in FIG. 2.

In one presently preferred embodiment of this invention, it has been found desirable to incorporate thermoplastic fibers 38 into the center layer 50 so that such center layer 50 is formed of an intermixture of fibrous material 28, moisture-absorbent particles 36 and thermoplastic fibers 38 as schematically illustrated in FIGS. 2 and 2A. The purpose of adding the thermoplastic fibers 38 to this layer 50 is to help retain the moisture-absorbent particles 36 within such layer 50 and prevent their escape either completely out of the non-woven pad 30 or into the bottom and top sections 52, 54. This allows less fibrous material to be utilized in forming the non-woven pad 30 without reducing its moisture-absorbent capacity. Additionally, the thermoplastic fibers 38 increase the stability and structural integrity of the center layer 50, as well as the tear strength thereof, particularly when the non-woven pad 30 becomes wet during use.

The system for introducing thermoplastic fibers 38 into the intermediate or center layer 50 of non-woven pad 30 is schematically illustrated in FIG. 1. In the presently preferred embodiment, a thermoplastic material die head 56, described in detail below, is disposed at least partially within the interior of forming chamber and its discharge outlet 58 is oriented at approximately a 45° angle relative to the conveyor 18. The die head 56 is supplied with a polymeric binder material such as hot melt adhesive material from an adhesive spray gun 60 of the type disclosed in U.S. Pat. No. 4,785,996, owned by the same assignee as this invention, the disclosure of which is incorporated by reference in its entirety herein. The spray gun 60 is effective to supply adhesive continuously or intermittently to the die head 56 in response to signals from an adhesive supply and controller 62 of the type sold by Nordson Corporation of Amherst, Ohio, the assignee of this invention, under the name "Series 3700 Applicator". This adhesive supply and controller 62 is effective to supply molten hot melt adhesive to the spray gun 60, and to control the operation of the spray gun 60, so that adhesive is supplied to the die head 56 as required. The die head 56 is also supplied with heated air from an air heater 64 connected to an air supply 66. The air heater 64 is a commercially available unit, and one preferred type of air heater 64 is sold under the trade name "Chromolox" by Anderson Bohls Company of Cleveland, Ohio.

In the embodiment of FIGS. 1–2A, the thermoplastic material die head 56 is effective to introduce thermoplastic fibers 38 into the interior of forming chamber 12 for intermixture with the fibrous material 28 and moisture-absorbent particles 36 being drawn onto the conveyor 18 at the predetermined location 48. As viewed in FIG. 1, the thermoplastic material die head 56 is located above the spray gun 40, and is angled at about 45° relative to conveyor 18, such that the thermoplastic fibers 38 are directed toward the conveyor 18 and across the path of the moisture-absorbent particles 36 discharged from spray gun 40. This produces an intermediate or center layer 50 within the non-woven pad 30 consisting of an intermixture of fibrous material 28, moisture-absorbent particles 36 and thermoplastic fibers 38. As viewed in FIG. 2A, the thermoplastic fibers 38 preferably intertwine with the fibrous material 28 and particles 36, and bond thereto, which binds or retains the particles 36 to the fibrous material 28 and substantially prevents the migration of such particles 36 from the center layer 50. The remaining areas of the thickness of non-woven pad 30, i.e., bottom layer 52 and top layer 54, are maintained substantially free of both moisture-absorbent particles 36 and thermoplastic fibers 38.

EXAMPLE

One example of conditions under which a non-woven pad 30 is formed employing the method and apparatus described with reference to FIGS. 1 and 2 is given below. In this example, the forming chamber 12 is a "Nuova Red" vertical forming chamber, sold by Nuova Red Italiana S.P.A. of Gropello Cairoli, Italy, having a height or vertical dimension as viewed in FIG. 1 of about 50 inches and a width of about 15.5 inches. The Nuova Red vertical forming chamber is operated to manufacture a non-woven pad 30, specifically for disposable diapers, at a rate of about 250 diapers per minute. A venturi powder pump mounted to a feed hopper is connected to a conduit located about 24 inches from the base or inlet 14 of forming chamber 12 in essentially the same position as spray gun 40 illustrated in FIG. 1. The thermoplastic material die head 56 is positioned above the spray gun 40 and angled at approximately 45° relative to the conveyor 18 so that the thermoplastic fibers 38 discharged therefrom are directed toward a location about 15 inches in height from the bottom or inlet 14 of forming chamber 12. The system operating parameters are as follows:

| | |
|---|---|
| Fibrous Material Flow Rate: | 36 grams per diaper |
| Hot Melt Adhesive: | HL-6149X (polyamide) H. B. Fuller Company, Vadnais Heights, Minnesota |
| Adhesive Temperature: | 400° F. |
| Die Head Adhesive Pressure: | 80 psi |
| Die Head Adhesive Flow Rate: | 3.75 grams per diaper |
| Air Temperature: | 325-350° F. at die head |
| Die Head Air Pressure: | 20 psi |
| Moisture-Absorbent Material: | Kendal Superabsorbent Material, Kendal Company Boston, Massachusetts |
| Flow Rate Moisture-Absorbent Material: | 6 grams per diaper |

Under the foregoing conditions, a non-woven pad 30 is obtained having a bottom layer 52 of fibrous material 28, a center layer 50 of intermixed fibrous material 28, moisture-absorbent particles 36 and thermoplastic fibers 38, and a top layer 54 of fibrous material 28 wherein the bottom and top layers 52, 54 are substantially free of both moisture-absorbent particles 36 and thermoplastic fibers 38.

Figure 3:
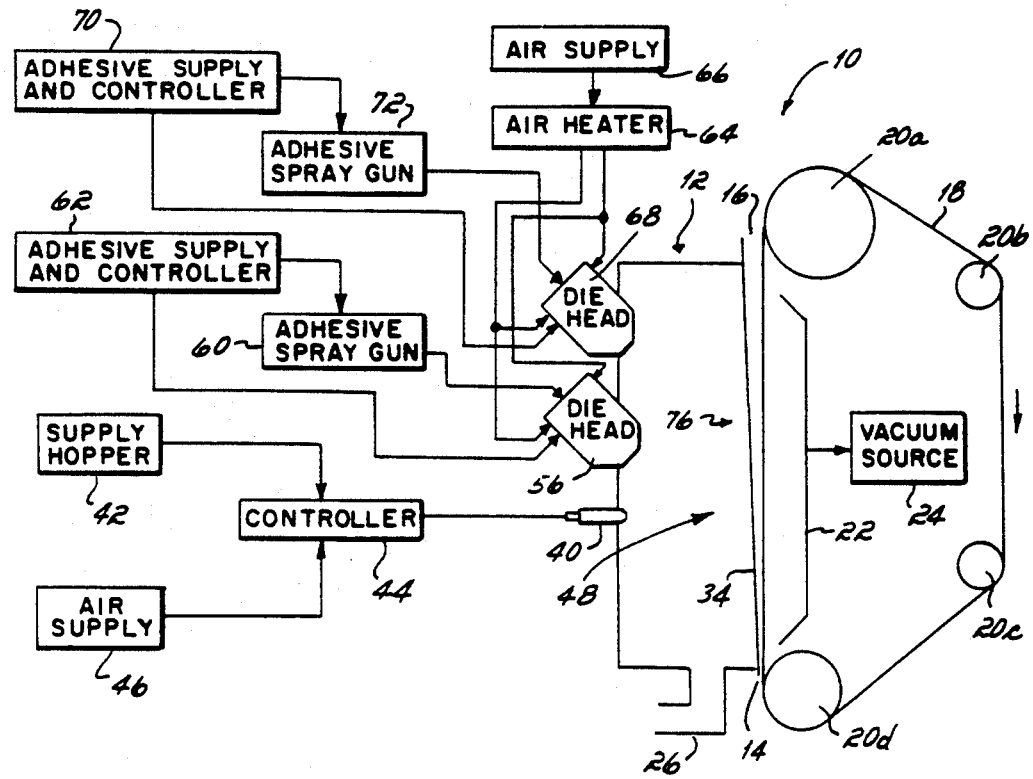
FIG. 3 is a schematic, elevational view of an alternative embodiment of the apparatus of this invention.
Figure 4:
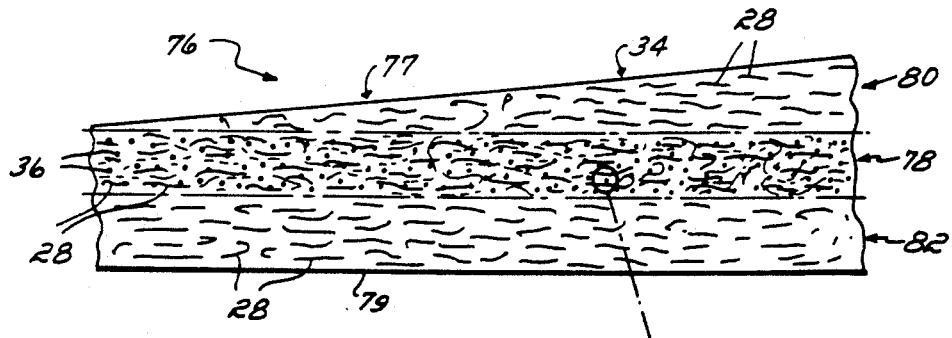
FIG. 4 is an enlarged, partial view of the non-woven pad formed with the apparatus of FIG. 3.
Figure 4A:
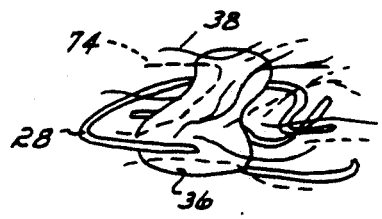
FIG. 4A is an enlarged, schematic view of the circled area in FIG. 4.

Referring now to FIGS. 3-4A, an alternative embodiment of the method of this invention is illustrated which employs the same apparatus 10 as described in connection with FIGS. 1-2A except for the addition of a second thermoplastic material die head 68 located at least partially within the interior of forming chamber 12 in a position to introduce thermoplastic fibers toward the predetermined location 48. In this embodiment, a second adhesive supply and controller 70 and a second adhesive spray gun 72 are associated with the second thermoplastic material die head 68, and this equipment is identical to the adhesive supply and controller 62 and spray gun 60 connected to thermoplastic material die head 56 illustrated in FIG. 3 and described above in connection with FIGS. 1 and 2.

The purpose of employing two separate die heads 56, 68, and their associated thermoplastic material supply equipment, is to introduce two different types of thermoplastic materials into a predetermined portion of the thickness of a non-woven pad 76, i.e., thermoplastic fibers 38 from die head 56 shown in solid lines in FIG. 4A and thermoplastic fibers 74 from second die head 68 shown in dotted lines in FIG. 4A. Preferably, the second die head 68 is located at least partially within the forming chamber 12 in position to introduce the thermoplastic fibers 74 at the predetermined location 48 relative to the conveyor 18 where the moisture-absorbent particles 36 are discharged from spray gun 40. A non-woven pad 76 is thus formed in the identical manner as described above in connection with the non-woven pad 30, having an angled top surface 77 and a bottom surface 79 resting on conveyor 18, except the non-woven pad 76 has an intermediate or center layer 78 formed of an intermixture of four materials, i.e., fibrous material 28, moisture-absorbent particles 36, thermoplastic fibers 38 and thermoplastic fibers 74. The top and bottom layers 80, 82, respectively, of non-woven pad 76 are maintained substantially free of moisture-absorbent particles 36 and thermoplastic fibers 38, 74 in the same manner described above in the embodiment of FIGS. 1 and 2.

The two types of thermoplastic fibers 38 and 74 introduced into the center or intermediate layer 78 of non-woven pad 76 are intended to produce specific properties in the center layer 78. Preferably, the thermoplastic fibers 38 are formed from a polymeric binder material such as a polyamide thermoplastic hot melt adhesive, or other suitable materials having relatively high tensile strength. Such thermoplastic fibers 38 impart additional strength, stability and tear resistance to the intermediate layer 78, particularly when the non-woven pad 76 becomes wet. The thermoplastic fibers 74 are preferably formed from a material such as polyethylene, polypropylene or other suitable types of thermoplastic binder materials which aid in retaining the "loft" of the intermediate layer 78. The thermoplastic fibers 74 formed of polyethylene material help maintain air gaps between the fibrous material 28 in the center layer 78 so that it retains a "fluff-like" consistency which is resistant to compression as, for example, when a baby sits on a disposable diaper made with a non-woven pad 76. Other than employing two die heads 56, 68 to discharge two different types of thermoplastic fibers 38 and 74, the embodiment of FIGS. 3 and 4 is essentially identical to that discussed above in connection with FIGS. 1 and 2.

Figure 5:
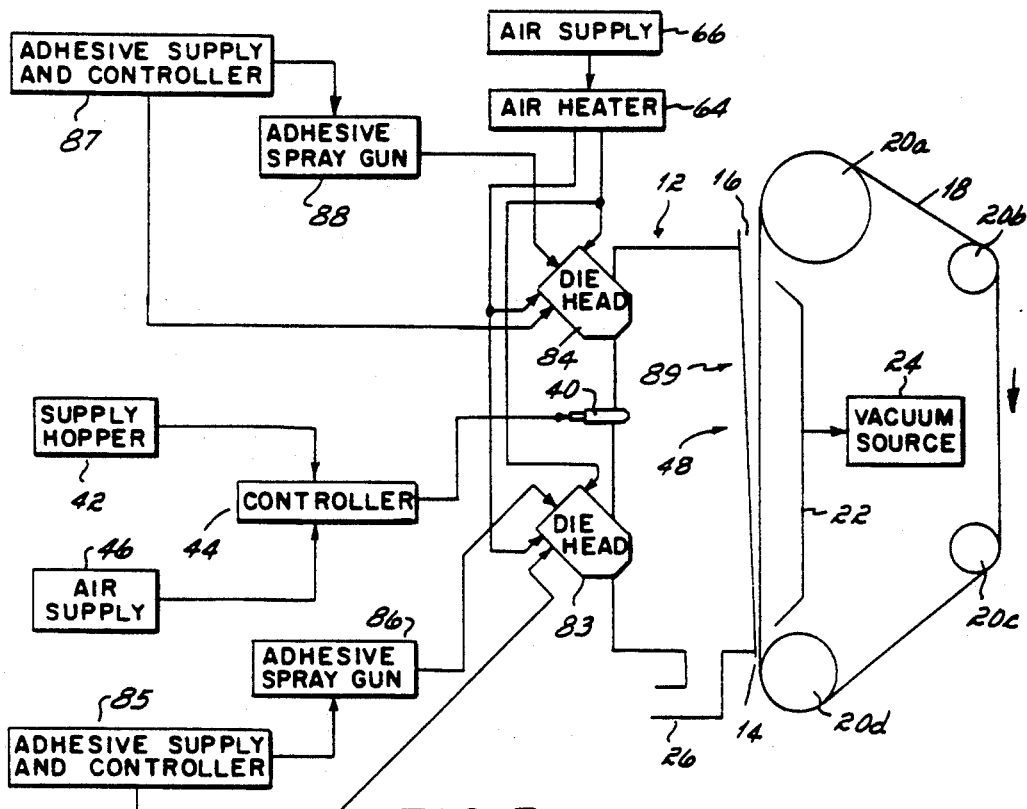
FIG. 5 is a schematic, elevational view of a still further embodiment of the apparatus of this invention.
Figure 6:
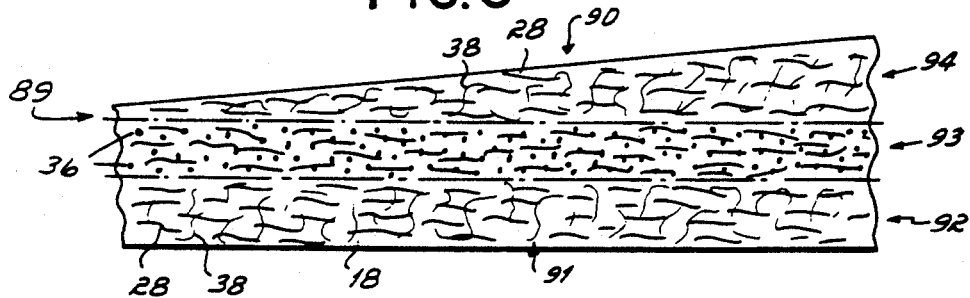
FIG. 6 is an enlarged, partial view of the non-woven pad formed in accordance with the apparatus of FIG. 5.

With reference to FIGS. 5 and 6, a still further embodiment of the method of this invention is illustrated. This embodiment is identical to the embodiment disclosed in FIGS. 1-2A, except a lower thermoplastic material die head 83 is located at least partially within the forming chamber 12 in a position upstream from or below the particle spray gun 40 and the predetermined location 48 as viewed in FIGS. 5 and 6, and an upper die head 84 is positioned at least partially within forming chamber 12 at a location above or downstream from the particle spray gun 40 and the predetermined location 48. Both of these die heads 83, 84 are identical to die heads 56 and 68, and are supplied with thermoplastic material in the same manner and with the same equipment depicted in FIGS. 1-4A. Preferably, die head 83 is supplied with thermoplastic material from an adhesive supply and controller 85 and spray gun 86, whereas die head 84 is supplied by adhesive supply and controller 87 and spray gun 88. In addition, fibrous material 28 is drawn onto the conveyor 18 in the embodiment of FIGS. 5 and 6 in the identical manner as described above to produce a non-woven pad 89 having an angled top surface 90 and a bottom surface 91 resting on conveyor 18. The difference in this embodiment, however, is that thermoplastic fibers and moisture-absorbent material are introduced at different locations within the thickness of the non-woven pad 89.

As viewed in FIGS. 5 and 6, the lower die head 83 is positioned with respect to the inlet 14 of forming chamber 12 to discharge thermoplastic fibers 38 toward the inlet 14 in the area where the non-woven pad 89 is just beginning to be formed. These thermoplastic fibers 38 intermix with fibrous material 28 being drawn onto the conveyor 18 at a location upstream from the predetermined location 48, thus forming a bottom layer 92 of intermixed fibrous material 28 and thermoplastic fibers 38. As the conveyor 18 continues moving through the forming chamber 12 to the predetermined location 48, moisture-absorbent particles 36 are discharged from particle spray gun 40 at the predetermined location 48 and these moisture-absorbent particles 36 intermix with the fibrous material 28 thereat to form a center layer 93 of intermixed fibrous material 28 and moisture-absorbent particles 36 atop the bottom layer 92. As the conveyor 18 continues its movement toward the outlet 16 of forming chamber 12, the upper thermoplastic material die head 84 discharges thermoplastic fibers 38 into an area between the predetermined location 48 where particle spray gun 40 is positioned and the outlet 16 of forming chamber 12. These thermoplastic fibers 38 from upper thermoplastic material die head 84 intermix with fibrous material 28 being drawn onto conveyor 18 downstream from predetermined location 48 to form a top layer 94 of intermixed fibrous material 28 and thermoplastic fibers 38 atop the intermediate layer 93.

As viewed in FIG. 6, the non-woven pad 89 thus comprises a bottom layer 92 of intermixed fibrous material 28 and thermoplastic fibers 38, and intermediate layer 93 of intermixed fibrous material 28 and moisture-absorbent particles 36 and a top layer 94 of intermixed fibrous material 28 and thermoplastic fibers 38. The bottom layer 92 and top layer 94 are intended to prevent or reduce the loss or migration of moisture-absorbent particles 36 from the interior of the non-woven pad 89. The thermoplastic fibers 38 within bottom layer 92 and top layer 94 are effective to resist the passage of moisture-absorbent particles 36 therethrough, but permit the passage of fluids into the intermediate layer 93 for absorption by the moisture-absorbent particles 36.

Figure 10A:
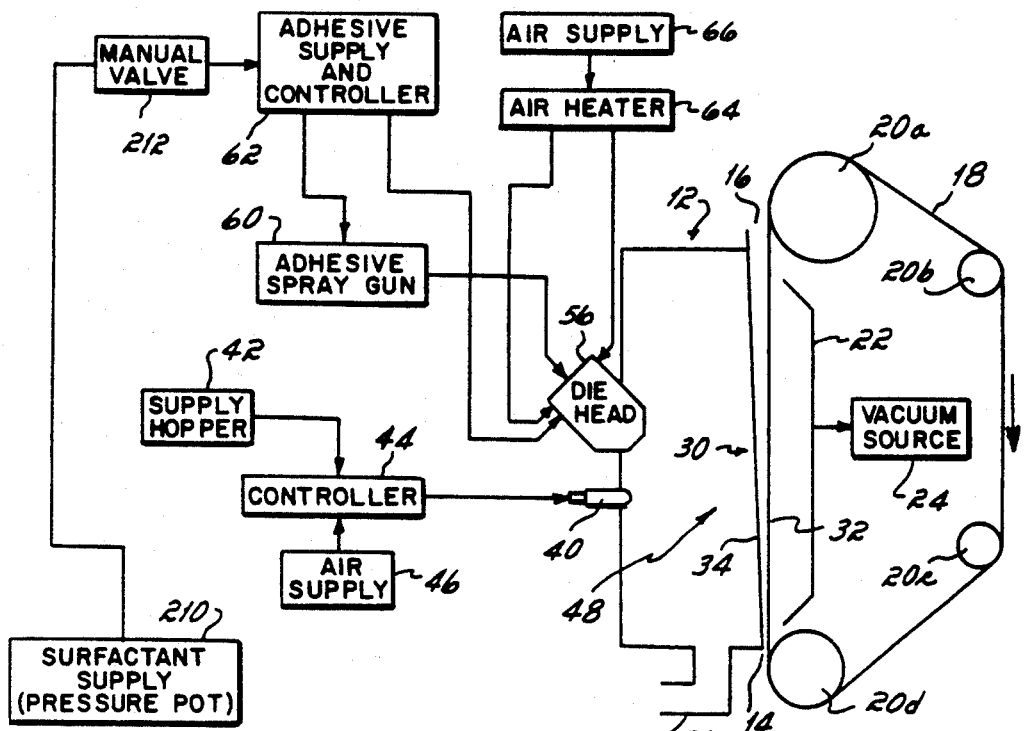
FIGS. 10A and 10B are schematic views, similar to FIG. 1, of alternative embodiments for introducing a surfactant onto the thermoplastic fibers discharged from the thermoplastic material die heads.
Figure 10B:
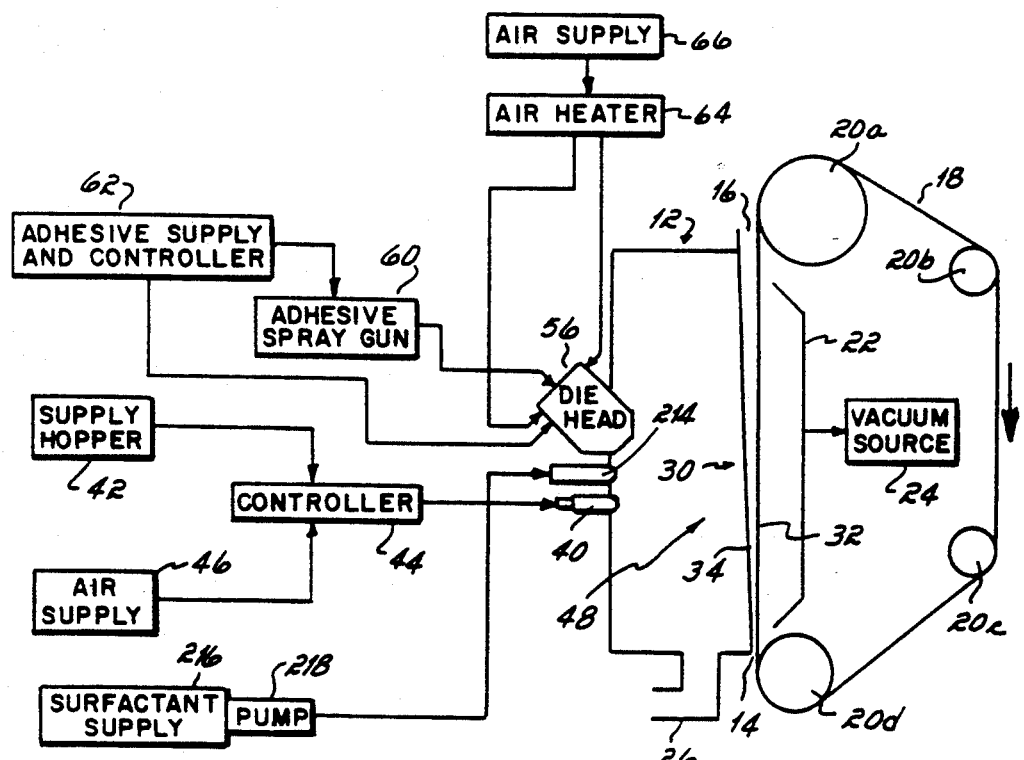

Referring now to FIGS. 10A-10D, further alternative embodiments of the method and apparatus of this invention are illustrated. FIGS. 10A and 10B each disclose an apparatus identical in structure and operation to that shown in FIG. 1, as described above, except for the addition of structure for positioning a moisture-wicking substance such as a surfactant at the exterior surface of the thermoplastic fibers 38 introduced into the forming chamber 12. Similarly, the embodiments shown in FIGS. 10C and 10D disclose apparatus identical in structure and operation to that illustrated in FIG. 5, as described above, except for the addition of structure to position a moisture-wicking substance at the exterior surface of the thermoplastic fibers 38 introduced into forming chamber 12.

It may be desirable in some applications to increase the wicking or moisture transfer capability of the thermoplastic fibers 38 so that moisture is more efficiently transferred to the moisture-absorbent particles 36 within the non-woven pad. The embodiments of FIGS. 10A and 10B form a non-woven pad 30, and the embodiments of FIGS. 10C and 10D form a non-woven pad 89, in the identical manner described above in connection with FIGS. 1 and 5, respectively. These pads 30, 89 each comprise bottom, center and top layers in which the moisture-absorbent material 36 is directed into the center layer and the thermoplastic fibers 38 are either directed into the center layer or into both the top and bottom layers, as described above. In both types of non-woven pads 30 and 89, a moisture-wicking substance such as a surfactant applied at the exterior surface of the thermoplastic fibers 38 may increase the wicking capability of such fibers 38 so that moisture entering the top, bottom or center layers of the non-woven pads 30, 89 is wicked or transferred by the fibers 38 to the moisture-absorbent particles 36 within the center layer thereof. This enhances the moisture-absorbent capacity of the non-woven pads 30, 89.

In the presently preferred embodiment, the term "moisture-wicking substance" is meant to refer to compositions such as surfactants or plasticizers, which, when present in an effective amount on the exterior surface of the thermoplastic fibers 38, are intended to increase the wicking or moisture transmitting capability of the thermoplastic fibers 38. One commercially available surfactant believed to be suitable is Tritan-X 100 manufactured by Rohm & Haas Company of Philadelphia, Pa. Examples of other moisture-wicking substances believed to be suitable include arylalkyd sulfates, polyethylene glycol, fatty acid esters, polyethers, phosphate esters, alkyd diethanolamines and glyceryl monostearates. For purposes of the present description, such moisture-wicking substances are referred to herein as "surfactants", it being understood that such term is used by way of example and is not intended to be restrictive of the types of moisture-wicking substances suitable for use.

Referring to FIGS. 10A and 10B, alternative embodiments are illustrated for positioning surfactant at the exterior surface of the thermoplastic fibers 38 introduced into the center layer 50 of non-woven pad 30. In FIG. 10A, a surfactant supply 210 is connected to the adhesive supply and controller 62 through a manually operated valve 212. Surfactant is allowed to intermix with the hot melt adhesive within the adhesive supply and controller 62, with the valve 212 in an open position, and this mixture or blend is transmitted to the die head 56. The die head 56 produces thermoplastic fibers 38 in which at least some of the surfactant is located on the exterior surface thereof, and these fibers 38 are discharged into the forming chamber 12. It is contemplated that the surfactant supply 210 is a pressure pot of the type sold commercially by Nordson Corporation of Amherst, Ohio under Nordson Part No. 270,963. Alternatively, the surfactant could be supplied from a 55 gallon drum, for example, through a piston pump such as a Model 25B pump, manufactured by Nordson Corporation of Amherst, Ohio. Additionally, the manual valve 212 can be essentially any suitable type of commercially available valve, or, alternatively, an automatically operated valve such as a solenoid valve controlled by the adhesive supply and controller 62.

In the alternative embodiment shown in FIG. 10B, surfactant is introduced by a spray gun 214 directly into the forming chamber 12 in the path of the thermoplastic fibers 38 discharged from die head 56 so that the exterior surface of at least some of the thermoplastic fibers 38 is coated with the surfactant to increase their moisture-wicking capability. The spray gun 214 is supplied with surfactant by a surfactant supply 216 connected to a pump 218. Preferably, the spray gun 214 is a Model A7A airless spray gun sold by Nordson Corporation of Amherst, Ohio. The surfactant supply 216 and pump 218 can be any commercially available components suitable for use with surfactants, such as a drum and the Nordson Model 25B pump mentioned above.

Figure 10C:
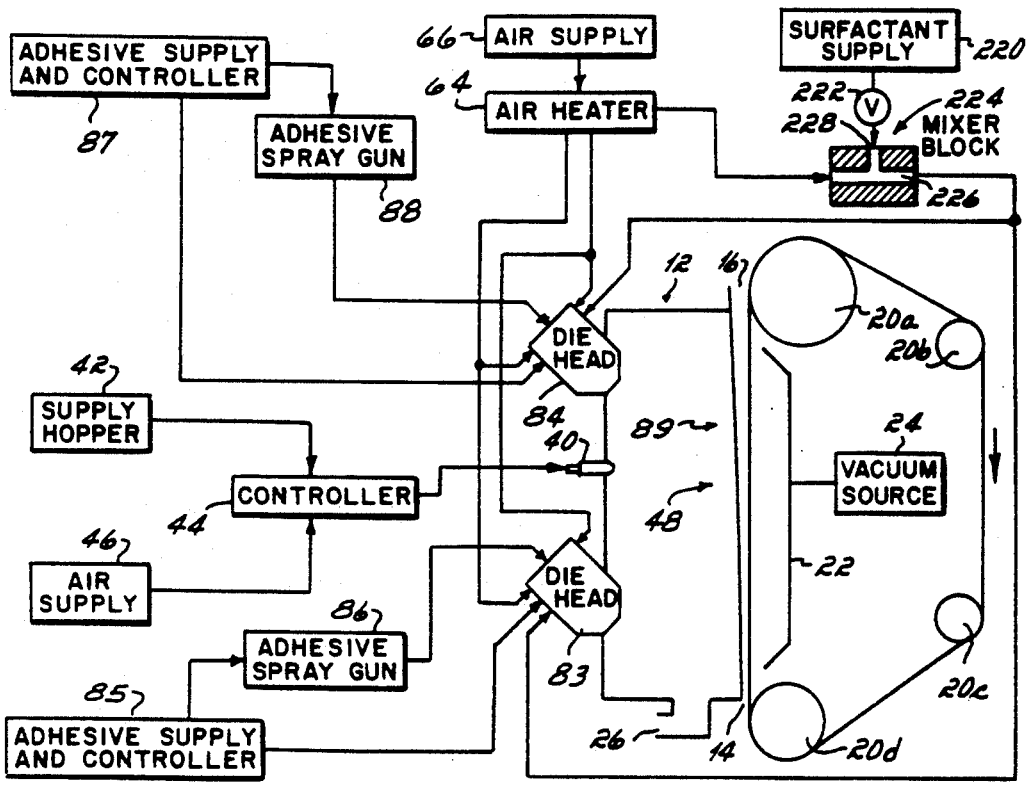
FIGS. 10C and 10D are schematic views, similar to FIG. 5, of alternative embodiments for introducing a surfactant onto the thermoplastic fibers discharged from the thermoplastic material die heads.
Figure 10D:
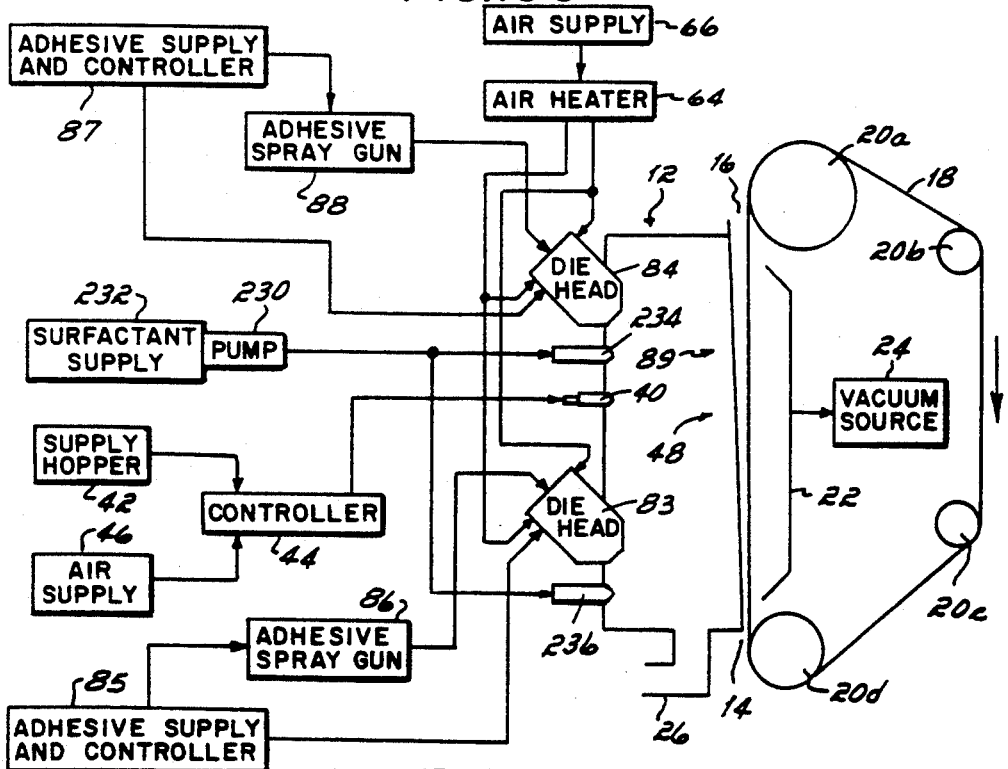

FIGS. 10C and 10D each disclose structure for positioning a surfactant at the exterior surface of the thermoplastic fibers 38 in the top and bottom layers 94, 92 of non-woven pad 89. In the embodiment of FIG. 10C, a surfactant supply 220 is connected by a line, carrying a valve 222 to a mixer block 224. The mixer block 224 is formed with a throughbore 226 connected to a transverse bore 228. One end of the throughbore 226 is connected to the air heater 64 and the transverse bore 228 is connected to the line from surfactant supply 210. The heated air and surfactant are intermixed within the mixer block 224 and discharged through the opposite end of throughbore 226 into a line which connects to each die head 83 and 84. The intermixed surfactant and heated air is then combined with the thermoplastic material within each die head 83, 84 to form a blend. Each of the die heads 83, 84 is effective to discharge thermoplastic fibers 38 into the non-woven pad 89, as described in connection with FIG. 5, wherein at least a portion of the surfactant is located or positioned at the exterior surface of the fibers 38 in an effective amount so that the moisture-wicking capability of the fibers 38 is increased.

A still further embodiment illustrating structure for introducing surfactant into the forming chamber 12 is illustrated in FIG. 10D. In this embodiment, a pump 230 is mounted to a surfactant supply 232 and is connected to a first spray gun 234 located near die head 84 and a second spray gun 236 located near die head 83. Each of these spray guns 234, 236 are preferably airless spray guns such as spray gun 214. The spray guns 234, 236 are effective to introduce surfactant into the interior of forming chamber 12 in the path of the thermoplastic fibers 38 discharged from die heads 84 and 83, respectively, so that the exterior surface of at least some of the fibers 238 become at least partially coated with surfactant to increase the moisture-wicking capability thereof.

Figure 9:
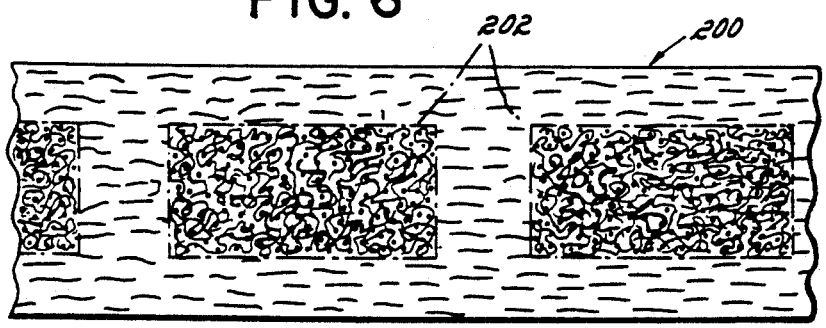
FIG. 9 is a plan view of a non-woven pad formed with longitudinally spaced areas of intermixed fibrous material, moisture-absorbent material and thermoplastic fibers.

Referring now to FIG. 9, a non-woven pad 200 is illustrated which includes a series of longitudinally spaced areas 202 of intermixed fibrous material 28, moisture-absorbent particles 36 and thermoplastic fibers 204 located within a portion of the thickness of the non-woven pad 200. This non-woven pad 200 can be formed with the equipment and method depicted in any of the embodiments illustrated in FIGS. 1-6 and 10A-10D, as desired. For example, employing the equipment and method depicted in FIG. 1, the longitudinally spaced areas 202 are formed of intermixed fibrous material 28, moisture-absorbent particles 36 and thermoplastic fibers 38 located approximately in the center of non-woven pad 202. In the embodiment of FIG. 3, the longitudinally spaced areas 202 are also located at the center of non-woven pad 200 but two types of thermoplastic fibers 38, 74 are intermixed with the fibrous material 28 and moisture-absorbent particles 36 thereat. The non-woven pad 200 made in accordance with the method and apparatus of FIG. 5 has longitudinally spaced areas 202 within the three layers of the pad, in vertical alignment with one another, wherein one area 202 at the bottom of the pad 200 includes intermixed fibrous material 28 and thermoplastic fibers 38, another area 202 at the center of pad 200 includes intermixed fibrous material 28 and moisture-absorbent particles 36 and a third area 202 at the top of the pad 200 includes intermixed fibrous material 28 and thermoplastic fibers 38.

The longitudinally spaced areas 202 in pad 200 formed in accordance with the method of each of the embodiments of FIGS. 1-6 are obtained by operating the spray gun 40 and the die heads 56, 68, 83 and/or 84 intermittently so that moisture-absorbent particles 36 and thermoplastic fibers 38 or 74 are introduced only in the longitudinally spaced areas 202 of pad 200. The controller 44 is operative to control the intermittent operation of spray gun 40, and the identical adhesive supply and controllers 62, 70, 85 and/or 87 are operative to control the supply of thermoplastic material to the die heads 56, 68, 83 and 84, respectively.

THERMOPLASTIC MATERIAL DIE HEAD

Figure 7:
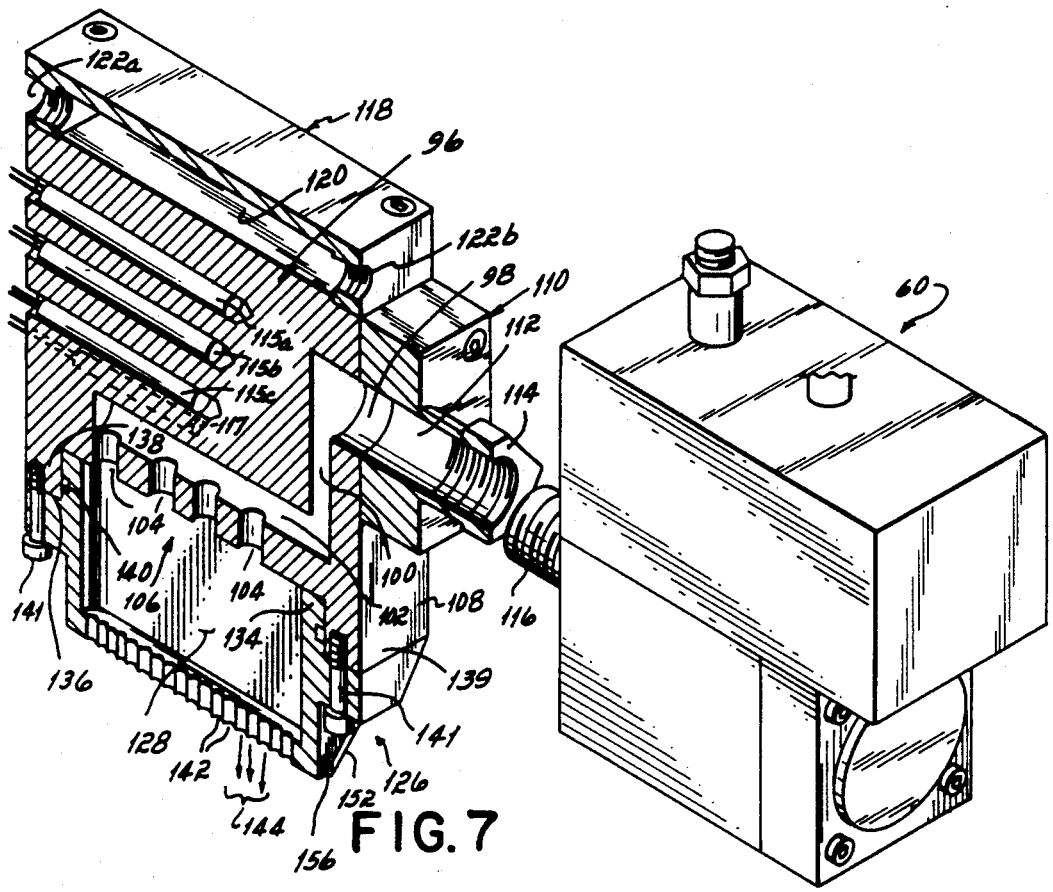
FIG. 7 is an elevational view in partial cross section of the thermoplastic material die head of this invention.
Figure 8:
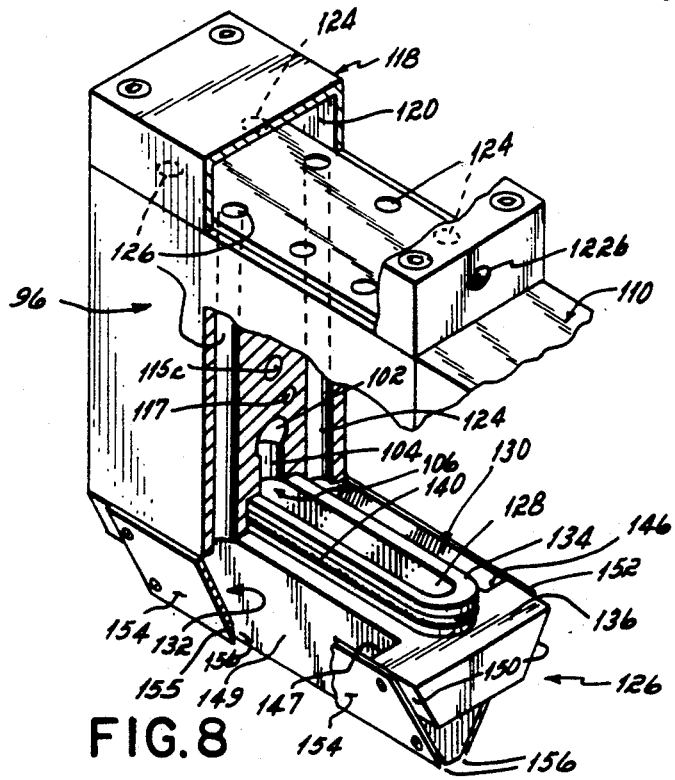
FIG. 8 is a cross sectional view of the thermoplastic material die head shown in FIG. 7, taken generally along line 8—8 thereof.

Referring now to FIGS. 7 and 8, the detailed structure of thermoplastic material die head 56, 68, 83 and 84, all of which are identical, is illustrated. Each of these thermoplastic material die heads comprises a die head body 96 formed with an adhesive inlet 98 which is connected by a vertical passage 100 to a transfer passage 102. This transfer passage 102 is connected to four ports 104 formed at the base 106 of die head body 96. In the presently preferred embodiment, the side wall 108 of die head body 96 mounts an adaptor plate 110 having a passage 112 which communicates with the adhesive inlet 98 in die head body 96. This adaptor plate 110 has a coupling 114 which mounts to the nozzle 116 of an adhesive dispenser gun such as dispenser 60 illustrated in FIG. 1. The adhesive dispenser 60 is effective to introduce the thermoplastic hot melt adhesive, continuously or intermittently as controlled by adhesive supply and controller 62, into the die head body 96 through the adaptor plate 110 and the adhesive inlet 98 in die head body 96. Preferably, the hot melt adhesive is maintained in a molten state by three heaters 115a–c, each carried within bores formed in the center portion of die head body 96 above transfer passage 102. An RTD 117 is also mounted in the die head body 96 near the heaters 115a–c to monitor the temperature thereat.

The top wall of die head body 96 as viewed in FIG. 7 mounts a rectangular-shaped air cap 118 having a hollow interior forming an air chamber 120. Heated air is supplied into the air chamber 120 through ports 122a,b on either side thereof, each of which are connected to the air heater 64 mentioned above. See FIG. 1. As best shown in FIG. 8, the heated air introduced into the air chamber 120 of air cap 118 is distributed into air passages 124, 126 formed in opposite sides of the die head body 96. Preferably, there are four air passages 124 on one side of die head body 96, and another four air passages 126 on the opposite side thereof.

In the presently preferred embodiment, the base 106 of die head body 96 mounts a nozzle block 126. The nozzle block 126 is formed with a center, hot melt discharge plenum 128 and two air plenums 130, 132 located on either side of the hot melt discharge plenum 128. The hot melt discharge plenum 128 has an oval-shaped projection 134 which rests against the base 106 of die head body 96 so that the adhesive ports 104 in the die head body 96 communicate with the interior of hot melt discharge plenum 128 in the nozzle block 126. This projection 134 forms a shoulder 136 which mounts downwardly projecting flanges 138, 139 formed on each end of the base 106 of die head body 96. Preferably, an O-ring 140 is interposed between the flanges 138, 139 and projection 134 to form a fluid-tight seal therebetween. The nozzle block 126 and die head body 96 are preferably interconnected by screws 141.

As viewed in FIG. 7, the bottom portion of the hot melt discharge plenum 128 in nozzle block 126 is formed with a plurality of discharge outlets 142 located side-by-side along the length of the hot melt discharge plenum 128. Each of these discharge outlets 142 is effective to eject a separate strand 144 of thermoplastic hot melt adhesive, as depicted by the arrows in FIG. 7. The hot melt adhesive is transmitted to the discharge outlets 142 by the above described adhesive flow path, i.e., adhesive is first introduced from the adhesive spray gun 60 into the passage 112 of adaptor plate 110 where it flows into the adhesive inlet 98 of die head body 96. The adhesive is directed through the vertical passage 100 of die head body 96 to the transfer passage 102. Each of the ports 104 at the base 106 of die head body 96 connected to transfer passage 102, in turn, transmit the adhesive into the hot melt discharge plenum 128 of nozzle block 126 from which it is ejected through the discharge outlets 142.

In order to form the adhesive strands 144 into thermoplastic fibers 38, the adhesive strands 144 are impacted with a jet or fan of heated air after they are ejected from discharge outlets 142. As viewed in FIG. 8, opposite sides of the nozzle block 126 are formed with recesses 146, 147, respectively, each having an inner wall 149 and an angled outer wall 150. A cover plate 152 is mounted to the angled outer wall 150 over recess 146 and a cover plate 154 is mounted over the angled outer wall 150 over recess 147 to form the air plenums 130, 132, respectively. Each of the plates 152, 154 is formed with a longitudinally extending slot 155 in their bottom interior surfaces which form elongated discharge openings 156 at the base of each air plenum 130 and 132. The size of these discharge openings 156 can be varied, as desired, by employing plates 152 or 154 having longitudinal slots 155 of different size.

Heated air entering the air chamber 120 of air cap 118 in die head body 96 is thus transmitted through the air passages 124, 126 on either side of die head body 96 into the air plenums 130 and 132. Because the cover plates 152, 154 are mounted at an angle relative to the inner walls 149 of air plenums 130, 132, the heated air discharged through the discharge opening 156 in each air plenum 130, 132 is directed at an angle relative to the path of the adhesive strands 144 ejected from discharge outlets 142 of hot melt discharge plenum 128. An essentially continuous stream or fan of heated air, emitted from the elongated discharge slots 156 of air plenums 130, 132, impacts the adhesive strands 144 and attenuates the adhesive to form elongated, strand-like thermoplastic fibers 38. These thermoplastic fibers 38 are directed by the force of the heated air emitted from air plenums 130, 132 into the interior of forming chamber 12 for combination with the fibrous material 28 and/or moisture-absorbent particles 36 as described in detail above.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

For example, certain types of thermoplastic, polymeric binder materials are mentioned above for combination at various locations within the thickness of the non-woven pad formed in accordance with the method of this invention. It is contemplated, however, that other types of thermoplastic binder materials could be employed to achieve the same or different characteristics of the non-woven pad as desired. The particular types of thermoplastic materials mentioned herein are thus not intended to be restrictive, it being understood that other types of materials could be injected at various, discreet locations along the non-woven pad formed within the forming chamber 12, as desired.

Additionally, it should be understood that the various embodiments shown in FIGS. 10A-10D for introducing surfactant as a coating for the thermoplastic fibers are essentially interchangeable with one another and can be used with the embodiment of FIG. 3. For example, the surfactant supply 210 and valve 212 shown in FIG. 10A can also be employed to introduce surfactant into the adhesive supply and controllers 62, 70 of FIG. 3 and/or the adhesive supply and controllers 85, 87 of FIG. 5. Similarly, the mixer head 224 and associated structure illustrated in FIG. 10C can be employed to supply surfactant to the die head 56 of FIG. 1 and/or the die heads 56, 68 of FIG. 3.

Further, while the method and apparatus of this invention have been illustrated in connection with a vertical forming chamber 12, it should be understood that other types of forming chambers could be utilized and are considered within the scope of this invention. For example, horizontal forming chambers can be utilized as well as forming chambers of the general type disclosed in United Kingdom Patent Application 2,150,033A wherein a drum having circumferentially spaced pad forming pockets is rotatably mounted within a forming chamber and is movable between stations at which fibrous material and/or moisture absorbent material are drawn into the pockets on the drum.

Therefore, it is intended that the invention not be limited to the particular embodiment disclosed as the best mode contemplated for carrying out this invention, but that the invention will include all embodiments falling within the scope of the appended claims.

We claim:

1. Apparatus for forming a non-woven pad of fibrous material with a first material and a thermoplastic material interspersed throughout a selected portion of the thickness of said non-woven pad, comprising:

a forming chamber having an interior;

pad support means for supporting said non-woven pad, said pad support means being movable in a first direction within said interior of said forming chamber;

means for introducing fibrous material into said interior of said forming chamber;

vacuum means for applying a vacuum to draw said fibrous material onto said pad support means, said fibrous material forming said non-woven pad on said pad support means which increases in thickness in said first direction of movement of said pad support means;

first dispenser means for intermixing said first material with a portion of said fibrous material being drawn onto said pad support means at a predetermined location within said forming chamber;

second dispenser means for forming thermoplastic fibers from said thermoplastic material and for dispensing said thermoplastic fibers into said forming chamber for intermixing with said first material and said fibrous material being drawn onto said pad support means at said predetermined location to form a layer of intermixed fibrous material, first material and thermoplastic fibers within a predetermined portion of said thickness of said non-woven pad while maintaining another portion of said thickness of said non-woven pad substantially free of said first material and said thermoplastic fibers.

2. The apparatus of claim 1 in which said pad support means is a conveyor.

3. Apparatus for forming a non-woven pad of fibrous material with a first material, a thermoplastic material and a third material interspersed throughout a selected portion of the thickness of said non-woven pad, comprising:

a forming chamber having an interior;

pad support means for supporting said non-woven pad, said pad support means being movable in a first direction within said interior of said forming chamber;

means for introducing fibrous material into said interior of said forming chamber;

vacuum means for applying a vacuum to draw said fibrous material onto said pad support means, said fibrous material forming said non-woven pad on said pad support means which increases in thickness in said first direction of movement of said pad support means;

first dispenser means for intermixing said first material with a portion of said fibrous material being drawn onto said pad support means at a predetermined location within said interior of said forming chamber;

second dispenser means for forming thermoplastic fibers from said thermoplastic material and for dispensing said thermoplastic fibers into said forming chamber for intermixing with said first material and said fibrous material being drawn onto said pad support means at said predetermined location;

third dispenser means for intermixing a third material with said fibrous material, first material and thermoplastic fibers being drawn onto said pad support means at said predetermined location to form a layer of intermixed fibrous material, first material, thermoplastic fibers and third material within a predetermined portion of said thickness of said non-woven pad while maintaining another portion of said thickness of said non-woven pad substantially free of said first material, thermoplastic fibers and third material.

4. The apparatus of claim 3 in which said pad support means is a conveyor.

5. Apparatus for forming a non-woven pad of fibrous material with a first material, a thermoplastic material and a third material interspersed throughout selected portions of the thickness of said non-woven pad, comprising:

a forming chamber having an interior;

a pad support means for supporting said non-woven pad, said pad support means being movable in a first direction within said interior of said forming chamber;

means for introducing fibrous material into said interior of said forming chamber;

means for introducing fibrous material into said interior of said forming chamber;

vacuum means for applying a vacuum to draw said fibrous material onto said pad support means, said fibrous material forming said non-woven pad on said pad support means which increases in thickness in said first direction of movement of said pad support means;

first dispenser means for intermixing said first material with a portion of said fibrous material being drawn onto said pad support means at a predetermined location within said interior of said forming chamber;

second dispenser means for forming thermoplastic fibers from said thermoplastic material and for dispensing said thermoplastic fibers into said forming chamber for intermixing with said fibrous material being drawn onto said pad support means at a location upstream from said predetermined location;

third dispenser means for intermixing said third material with said fibrous material being drawn onto said pad support means at a location downstream from said predetermined location, whereby said non-woven pad is formed with a first layer of intermixed fibrous material and thermoplastic fibers which is drawn onto said pad support means upstream from said predetermined location, a second layer of intermixed fibrous material and said first material which is drawn atop said first layer at said predetermined location, and a third layer of intermixed fibrous material and said third material which is drawn atop said second layer downstream from said predetermined location.

6. The apparatus of claim 5 in which said pad support means is a conveyor.

7. Apparatus for forming a non-woven pad of fibrous material with a first material and a thermoplastic material interspersed throughout a selected portion of the thickness of said non-woven pad, comprising:

a chamber having an inlet and an outlet;

a conveyor movable between said inlet and said outlet of said chamber, said conveyor having a first side and a second side;

means for introducing fibrous material into said chamber;

vacuum means located on said first side of said conveyor for applying a vacuum in said chamber to draw said fibrous material onto said second side of said conveyor, said fibrous material forming a non-woven pad on said second side of said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;

first dispenser means for intermixing said first material with a portion of said fibrous material being drawn onto said conveyor at a predetermined location relative to said upwardly sloping top surface of said non-woven pad;

second dispenser means for forming thermoplastic fibers from said thermoplastic material and for dispensing said thermoplastic fibers into said chamber for intermixing with said first material and said fibrous material being drawn onto said conveyor at said predetermined location to form a layer of intermixed fibrous material, first material and thermoplastic fibers within a predetermined portion of said thickness of said non-woven pad while maintaining another portion of said thickness of said non-woven pad substantially free of said first material and said thermoplastic fibers.

8. The apparatus of claim 7 in which said second dispenser means comprises:
  a die head formed with at least one first passageway for transmitting thermoplastic material, and at least one second passageway for transmitting air;
  a nozzle block formed with a first discharge plenum having a plurality of discharge outlets and at least one second discharge plenum having an outlet oriented at an angle relative to the axes of said discharge outlets, said nozzle block being mounted to said die head so that said first passageway transmits said thermoplastic material into said first discharge plenum and through said discharge outlets thereof, and so that said second passageway transmits air into said second discharge plenum and through said outlet thereof for engagement with said thermoplastic material ejected from said discharge outlets.

9. The apparatus of claim 8 in which said at least one first passageway of said die head includes an inlet passageway, a transfer passageway connected to said inlet passageway and a number of discharge ports each connected between said transfer passageway and said first discharge plenum in said nozzle block.

10. The apparatus of claim 8 in which said first discharge plenum is formed at the center of said nozzle block, and said at least one second discharge plenum comprises two air plenums located on opposite sides of said first discharge plenum, each of said air plenums being defined by a recess formed in one side of said nozzle block and a plate connected to said nozzle block over said recess.

11. The apparatus of claim 8 in which said die head is formed with an air chamber adapted to communicate with a source of air, said at least one second passageway of said die head including a group of discharge passageways located on one side of said die head and another group of discharge passageways located on the other side of said die head, each of said groups of discharge passageways extending between said air chamber and one of said air plenums formed in said nozzle block.

12. Apparatus for forming a non-woven pad of fibrous material with a first material, a thermoplastic material interspersed throughout a selected portion of the thickness of said non-woven pad at spaced locations therealong, comprising:
  a chamber having an inlet and an outlet;
  a conveyor movable between said inlet and said outlet of said chamber, said conveyor having a first side and a second side;
  means for introducing fibrous material into said chamber;
  vacuum means on said first side of said conveyor for applying a vacuum in said chamber to draw said fibrous material onto said second side of said conveyor, said fibrous material forming said non-woven pad on said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;
  first dispenser means for intermittently mixing said first material with a portion of said fibrous material being drawn onto said conveyor at a predetermined location relative to said upwardly sloping top surface of said non-woven pad;
  second dispenser means for forming thermoplastic fibers from said thermoplastic material and for intermittently dispensing said thermoplastic fibers into said chamber for mixing with said first material and said fibrous material being drawn onto said conveyor at said predetermined location to form a layer of intermixed fibrous material, first material and thermoplastic fibers within a predetermined portion of said thickness of said non-woven pad at spaced locations therealong while maintaining another portion of said thickness of said non-woven pad at spaced locations therealong substantially free of said first material and said thermoplastic fibers.

13. Apparatus for forming a non-woven pad of fibrous material with a first material and a thermoplastic material interspersed throughout a selected portion of the thickness of said non-woven pad, comprising:
  a chamber having an inlet and an outlet;
  a conveyor movable between said inlet and said outlet of said chamber, said conveyor having a first side and a second side;
  means for introducing fibrous material into said chamber;
  vacuum means located on said first side of said conveyor for applying a vacuum in said chamber to draw said fibrous material onto said second side of said conveyor, said fibrous material forming a non-woven pad on said conveyor which increases in thickness in a direction from said inlet of said chamber toward said outlet thereof, said non-woven pad having a bottom surface resting on said conveyor and a top surface which slopes upwardly relative to said conveyor from said inlet of said chamber toward said outlet thereof;
  first dispenser means for intermixing said first material with a portion of said fibrous material being drawn onto said conveyor at a predetermined location relative to said upwardly sloping top surface of said non-woven pad;
  second dispenser means for forming thermoplastic fibers from said thermoplastic material and for dispensing said thermoplastic fibers into said forming chamber for intermixing with said first material and said fibrous material being drawn onto said conveyor at said predetermined location to form a layer of intermixed fibrous material, first material and thermoplastic fibers within a predetermined portion of said thickness of said non-woven pad while maintaining another portion of said thickness of said non-woven pad substantially free of said first material and said thermoplastic fibers;
  means for supplying said thermoplastic fibers to said second dispenser means;
  control means for controlling the operation of said second dispenser means.

14. The apparatus of claim 13 in which said second dispenser means comprises:
  a die head formed with at least one first passageway for transmitting said thermoplastic material, and at least one second passageway for transmitting air;
  a nozzle block formed with a first discharge plenum having a plurality of discharge outlets and at least one second discharge plenum having an outlet oriented at an angle relative to the axes of said discharge outlets, said nozzle block being mounted to said die head so that said first passageway transmits said thermoplastic material into said first discharge plenum and through said discharge outlets thereof, and so that said second passageway transmits air into said second discharge plenum and through said outlet thereof for engagement with said thermoplastic material ejected from said discharge outlets.

15. The apparatus of claim 13 in which said thermoplastic material is thermoplastic, hot melt adhesive, said means for supplying said thermoplastic hot melt adhesive to said second dispenser means comprising an adhesive spray gun connected to a source of molten hot melt adhesive material, said adhesive spray gun discharging hot melt adhesive material into said first passageway of said die head of said second dispenser means.

16. The apparatus of claim 15 in which said control means is an adhesive applicator operatively connected to said adhesive spray gun, said adhesive applicator being effective to open said adhesive spray gun to permit the passage of hot melt adhesive material into said die head and to close said adhesive spray gun to terminate the flow of hot melt adhesive material into said die head.

17. Apparatus for use with a forming chamber having an inlet and an outlet, a conveyor movable between said inlet and said outlet, a vacuum device located on one side of said conveyor for applying a vacuum in said chamber to draw fibrous material introduced into said chamber onto the opposite side of said conveyor forming a non-woven pad on said conveyor which has a bottom surface resting on said conveyor and a top surface which slopes upwardly relative to said conveyor from said inlet of said chamber to said outlet thereof, said apparatus comprising:
- first dispenser means for intermixing moisture-absorbent material with a portion of said fibrous material being drawn into said conveyor at a predetermined location relative to said upwardly sloping top surface of said non-woven pad;
- supply means for supplying hot melt adhesive material;
- second dispenser means connected to said supply means to receive said hot melt adhesive material;
- control means for causing said second dispenser means to form and dispense hot melt adhesive fibers into said forming chamber for intermixing with said moisture-absorbent material and said fibrous material being drawn onto said conveyor at said predetermined location to form a layer of intermixed fibrous material, moisture-absorbent material and hot melt adhesive fibers within a predetermined portion of said thickness of said non-woven pad while maintaining another portion of said thickness of said non-woven pad substantially free of said moisture-absorbent material and said hot melt adhesive fibers.

18. The apparatus of claim 17 in which said second dispenser means comprises:
- a die head formed with at least one first passageway for transmitting said hot melt adhesive material, and at least one second passageway for transmitting air;
- a nozzle block formed with a first discharge plenum having a plurality of discharge outlets and at least one second discharge plenum having an outlet oriented at an angle relative to the axes of said discharge outlets, said nozzle block being mounted to said die head so that said first passageway transmits said hot melt adhesive material into said first discharge plenum and through said discharge outlets thereof, and so that said second passageway transmits air into said second discharge plenum and through said outlet thereof for engagement with said hot melt adhesive material ejected from said discharge outlets.

19. The apparatus of claim 18 in which said means for supplying hot melt adhesive material to said second dispenser means comprises an adhesive spray gun connected to a source of molten hot melt adhesive material, said adhesive spray gun discharging hot melt adhesive material into said first passageway of said die head.

20. The apparatus of claim 19 in which said control means is an adhesive applicator operatively connected to said adhesive spray gun, said adhesive applicator being effective to open said adhesive spray gun to permit the passage of hot melt adhesive material into said die head and to close said adhesive spray gun to terminate the flow of hot melt adhesive material into said die head.

21. Apparatus for forming a non-woven pad of a fibrous material with a first material and a thermoplastic material interspersed throughout a selected portion of the thickness of said non-woven pad, comprising:
- a chamber having an inlet and an outlet;
- a conveyor movable between said inlet and said outlet of said chamber, said conveyor having a first side and a second side;
- means for introducing fibrous material in suspension into said chamber;
- vacuum means located on said first side of said conveyor for applying a vacuum in said chamber to draw said fibrous material onto said second side of said conveyor, said fibrous material forming a non-woven pad on said conveyor which has a minimum thickness at said inlet of said chamber and which increases in thickness toward said outlet thereof as more of said fibrous material is drawn onto said conveyor;
- first dispenser means for intermixing said first material with a portion of said fibrous material being drawn onto said conveyor at a predetermined location intermediate said inlet and outlet of said chamber;
- second dispenser means for forming thermoplastic fibers from said thermoplastic material and for dispensing said thermoplastic fibers into said chamber for intermixing with said first material and said first material being drawn onto said conveyor at said predetermined location, whereby said non-woven pad is formed with a bottom layer of said fibrous material which is drawn onto said conveyor between said inlet of said chamber and said predetermined location, an intermediate layer of intermixed fibrous material, first material and thermoplastic fibers which is drawn atop said bottom layer of fibrous material at said predetermined location, and a top layer of fibrous material which is drawn onto said intermediate layer between said predetermined location and said outlet of said chamber, said bottom layer and said top layer of said non-woven pad being substantially free of said first material and said thermoplastic fibers.

22. The apparatus of claim 21 in which said first and second dispenser means are operative intermittently to intermix said first material and said thermoplastic fibers with a portion of said fibrous material being drawn onto said conveyor at said predetermined location to form said intermediate layer of intermixed fibrous material, first material and thermoplastic fibers within a predetermined portion of the thickness of said non-woven pad at spaced locations therealong.

23. The apparatus of claim 21 in which said first dispenser means is a spray gun which discharges highly moister-absorbent material.

24. The apparatus of claim 21 in which said dispenser means is a thermoplastic material die head which discharges said thermoplastic fibers.

25. Apparatus for forming a non-woven pad of fibrous material with a first material, a thermoplastic material and a third material interspersed throughout a selected portion of the thickness of said non-woven pad, comprising:
  a chamber having an inlet and an outlet;
  a conveyor movable between said inlet and said outlet of said chamber, said conveyor having a first side and a second side;
  means for introducing fibrous material into said chamber;
  vacuum means located on said first side of said conveyor for applying a vacuum in said chamber to draw said fibrous material onto said second side of said conveyor, said fibrous material forming a non-woven pad on said second side of said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;
  first dispenser means for intermixing said first material with a portion of said fibrous material being drawn onto said conveyor at a predetermined location relative to said upwardly sloping top surface of said non-woven pad;
  second dispenser means for forming thermoplastic fibers from said thermoplastic material and for dispensing said thermoplastic fibers into said chamber for intermixing with said first material and said fibrous material being drawn onto said conveyor at said predetermined location;
  third dispenser means for intermixing said third material with said fibrous material, first material and said thermoplastic fibers being drawn onto said conveyor at said predetermined location to form a layer of intermixed fibrous material, first material, thermoplastic fibers and third material within a predetermined portion of said thickness of said non-woven pad while maintaining another portion of said thickness of said non-woven pad substantially free of said first material, thermoplastic fibers and said third material.

26. The apparatus of claim 25 in which said first dispenser means is a spray gun which discharges highly moisture-absorbent material.

27. The apparatus of claim 25 in which said second dispenser means is a thermoplastic material die head which discharges thermoplastic fibers having relatively high tensile strength.

28. The apparatus of claim 25 in which said third dispenser means is a thermoplastic material die head which discharges a thermoplastic material which maintains air gaps between said fibrous material within said intermediate layer of said non-woven pad.

29. Apparatus for forming a non-woven pad of fibrous material with a first material, a thermoplastic material and a third material interspersed throughout a selected portions of the thickness of said non-woven pad, comprising:
  a chamber having an inlet and an outlet;
  a conveyor movable between said inlet and said outlet of said chamber, said conveyor having a first side and a second side;
  means for introducing fibrous material into said chamber;
  vacuum means located on said first side of said conveyor for applying a vacuum in said chamber to draw said fibrous material onto said second side of said conveyor, said fibrous material forming a non-woven pad on said second side of said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;
  first dispenser means for intermixing said first material with a portion of said fibrous material being drawn onto said conveyor at a predetermined location relative to said upwardly sloping top surface of said non-woven pad;
  second dispenser means for forming thermoplastic fibers from said thermoplastic material and for dispensing thermoplastic fibers into said chamber for intermixing with said fibrous material being drawn onto said conveyor at a location upstream from said predetermined location;
  third dispenser means for intermixing said third material with said fibrous material being drawn onto said conveyor at a location downstream from said predetermined location, whereby said non-woven pad is formed with a first layer of intermixed fibrous material and thermoplastic fibers which is drawn onto said conveyor upstream from said predetermined location, a second layer of intermixed fibrous material and said first material which is drawn atop said first layer at said predetermined location, and a third layer of intermixed fibrous material and said third material which is drawn atop said second layer downstream from said predetermined location.

30. The apparatus of claim 29 in which said first dispenser means is a spray gun which discharges highly moisture-absorbent particulate material.

31. The apparatus of claim 29 in which said second dispenser means is a thermoplastic material die head which discharges said thermoplastic fibers.

32. The apparatus of claim 29 in which said third dispenser means is a thermoplastic material die head which discharges thermoplastic material.

33. Apparatus for forming a non-woven pad of fibrous material with a first material and a thermoplastic material interspersed throughout a selected portion of the thickness of said non-woven pad, comprising:
  a chamber having an inlet and an outlet;
  a conveyor movable between said inlet and said outlet of said chamber, said conveyor having a first side and a second side;

means for introducing fibrous material into said chamber;

vacuum means located on said first side of said conveyor for applying a vacuum in said chamber to draw said fibrous material onto said second side of said conveyor, said fibrous material forming a non-woven pad on said second side of said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;

first dispenser means for intermixing said first material with a portion of said fibrous material being drawn onto said conveyor at a predetermined location relative to said upwardly sloping top surface of said non-woven pad;

second dispenser means for forming thermoplastic fibers from said thermoplastic material and for dispensing thermoplastic fibers into said chamber for intermixing with said first material and said fibrous material being drawn onto said conveyor at said predetermined location;

means for positioning a moisture-wicking substance at the exterior surface of said second material in an effective amount so that said exterior surface of said thermoplastic fibers is capable of wicking moisture, whereby a layer of intermixed fibrous material, first material and thermoplastic fibers having a moisture-wicking substance at the exterior surface thereof is formed within a predetermined portion of said thickness of said non-woven pad while maintaining another portion of said thickness of said non-woven pad substantially free of said first material and said thermoplastic fibers.

34. The apparatus of claim 33 in which said means for positioning said moisture-wicking substance comprises means for applying said moisture-wicking substance to the exterior surface of said thermoplastic material.

35. The apparatus of claim 33 in which said means for positioning said moisture-wicking substance comprises means for intermixing said moisture-wicking substance and said thermoplastic material to from a blend in which at least a portion of said moisture-wicking substance is located at the exterior surface of said thermoplastic material.

36. The apparatus of claim 33 in which said second dispenser means is a thermoplastic material die head which discharges said thermoplastic fibers, said means for positioning said moisture-wicking substance at the exterior surface of said thermoplastic material comprising a mixer block adapted to connect to a source of air and to a source of the moisture-wicking substance, said mixer block being formed with a passageway for intermixing and then discharging said air and said moisture-wicking substance into said thermoplastic material die head for combination with thermoplastic material supplied to said die head, whereby said die head discharges thermoplastic fibers which are a blend of said thermoplastic material and said moisture-wicking substance wherein at least a portion of said moisture-wicking substance is located at the exterior surface of said thermoplastic fibers.

37. The apparatus of claim 33 in which said second dispenser means is a thermoplastic material die head which discharges said thermoplastic fibers, said means for positioning said moisture-wicking substance at the exterior surface of said thermoplastic material comprising means for intermixing thermoplastic material and moisture-wicking material to form a blend which is supplied to said die head, whereby said die head discharges thermoplastic fibers formed of said blend wherein at least a portion of said moisture-wicking substance is located at the exterior surface of said thermoplastic fibers.

38. The apparatus of claim 33 in which said means for positioning said moisture-wicking substance comprises a spray gun adapted to connect to a source of moisture-wicking substance, said spray gun discharging said moisture-wicking substance into said chamber in the path of said thermoplastic material so that said moisture-wicking substance is applied onto at least a portion of the exterior surface of said thermoplastic material.

39. Apparatus for use with a forming chamber having an inlet and an outlet, a conveyor movable between said inlet and said outlet, a vacuum device located on one side of said conveyor for applying a vacuum in said chamber to draw fibrous material introduced into said chamber onto the opposite side of said conveyor forming a non-woven pad on said conveyor which has a bottom surface resting on said conveyor and a top surface which slopes upwardly relative to said conveyor from said inlet of said chamber to said outlet thereof, said apparatus comprising:

first dispenser means for intermixing moisture-absorbent material with a portion of said fibrous material being drawn onto said conveyor at a predetermined location relative to said upwardly sloping top surface of said non-woven pad;

thermoplastic material supply means for supplying hot thermoplastic material;

means for transmitting a moisture-wicking substance to said thermoplastic material supply means for intermixing with said thermoplastic material to form a blend;

second dispenser means connected to said supply means to receive said blend of thermoplastic material and moisture-wicking substance;

control means for causing said second dispenser means to form thermoplastic fibers of said blend in which at least a portion of said moisture-wicking substance is located at the exterior surface of said fibers, and for discharging said thermoplastic fibers into said forming chamber for intermixing with said moisture-absorbent material and said fibrous material being drawn into said conveyor at said predetermined location to form a layer of intermixed fibrous material, moisture-absorbent material and fibers of thermoplastic material and a moisture-wicking substance within a predetermined portion of said thickness of said non-woven pad while maintaining another portion of said thickness of said non-woven pad substantially free of said moisture-absorbent material and said thermoplastic fibers.

40. The apparatus of claim 39 in which said means for transmitting a moisture-wicking substance comprises a pressure pot and a pump connected to said pressure pot which pumps said moisture-wicking substance into said thermoplastic material supply means.

41. Apparatus for forming a non-woven pad of fibrous material with a first material, a thermoplastic material and a third material interspersed throughout a selected portion of the thickness of said non-woven pad, comprising:

a chamber having an inlet and an outlet;

a conveyor movable between said inlet and said outlet of said chamber, said conveyor having a first side and a second side;

means for introducing fibrous material into said chamber;

vacuum means located on said first side of said conveyor for applying a vacuum in said chamber to draw said fibrous material onto said second side of said conveyor, said fibrous material forming a non-woven pad on said second side of said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;

first dispenser means for intermixing said first material with a portion of said fibrous material being drawn onto said conveyor at a predetermined location relative to said upwardly sloping top surface of said non-woven pad;

second dispenser means for forming thermoplastic fibers from said thermoplastic material and for dispensing said thermoplastic fibers into said chamber for intermixing with said first material and said fibrous material being drawn onto said conveyor at said predetermined location;

third dispenser means for intermixing a third material with said fibrous material, first material and thermoplastic fibers being drawn onto said conveyor at said predetermined location;

means for positioning a moisture-wicking substance at the exterior surface of at least one of said thermoplastic material and third material in an effective amount so that said exterior surface of said thermoplastic fibers formed from said thermoplastic material and said exterior surface of said third material are capable of wicking moisture, whereby a layer of intermixed fibrous material, first material, thermoplastic fibers, third material and moisture-wicking substance is formed within a predetermined portion of said thickness of said non-woven pad while maintaining another portion of said thickness of said non-woven pad substantially free of said first material, said thermoplastic fibers and said third material.

42. The apparatus of claim 41 in which said means for positioning said moisture-absorbing substance comprises means for applying said moisture-absorbing substance to the exterior surface of at least one of said thermoplastic material and said third material.

43. The apparatus of claim 41 in which said means for positioning said moisture-absorbing substance comprises means for intermixing said moisture-absorbing substance with at least one of said thermoplastic material and said third material to form a blend in which at least a portion of said moisture-absorbing substance is located at the exterior surface of at least one of said thermoplastic material and said third material.

44. The apparatus of claim 41 in which said second and third dispenser means are thermoplastic material die heads which discharge thermoplastic fibers, said means for positioning said moisture-wicking substance at the exterior surface of at least one of said thermoplastic material and said third material comprising a mixer block adapted to connect to a source of air and a source of moisture-wicking substance, said mixer block being formed with a passageway for intermixing and then discharging said air and moisture-wicking substance into said die head for combination with thermoplastic material supplied to said die head, whereby said die head discharges fibers with are a blend of said thermoplastic material and said moisture-wicking substance wherein at least a portion of said moisture-wicking substance is located at the exterior surface of said fibers.

45. The apparatus of claim 41 in which said means for positioning said moisture-wicking substance comprises a first spray gun and a second spray gun each adapted to connect to a source of moisture-wicking substance, said first spray gun discharging said moisture-wicking substance into said chamber in the path of said thermoplastic fibers so that said moisture-wicking substance is applied onto at least a portion of the exterior surface of said thermoplastic fibers, and said second spray gun discharging said moisture-wicking substance in the path of said third material so that said moisture-wicking substance is applied onto at least a portion of the exterior surface of said third material.

46. Apparatus for forming a non-woven pad of fibrous material with a first material, a thermoplastic material and a third material interspersed throughout selected portions of the thickness of said non-woven pad, comprising:

a chamber having an inlet and an outlet;

a conveyor movable between said inlet and said outlet of said chamber, said conveyor having a first side and a second side;

means for introducing fibrous material into said chamber;

vacuum means located on said first side of said conveyor for applying a vacuum in said chamber to draw said fibrous material onto said second side of said conveyor, said fibrous material forming a non-woven pad on said second side of said conveyor which increases in thickness in a direction from said inlet of said chamber toward said outlet thereof, said non-woven pad having a bottom surface resting on said second side of said conveyor and a top surface which slopes upwardly relative to said conveyor from said inlet of said chamber toward said outlet thereof;

first dispenser means for intermixing said first material with a portion of said fibrous material being drawn onto said conveyor at a predetermined location relative to said upwardly sloping top surface of said non-woven pad;

second dispenser means for forming thermoplastic fibers from said thermoplastic material and for dispensing said thermoplastic fibers into said chamber for intermixing with said fibrous material being drawn onto said conveyor at a location upstream from said predetermined location;

means for positioning a moisture-wicking substance at the exterior surface of said thermoplastic material in an effective amount so that said exterior surface of said thermoplastic fibers formed therefrom are capable of wicking moisture;

third dispenser means for intermixing said third material with said fibrous material being drawn onto said conveyor at a location downstream from said predetermined location;

means for positioning a moisture-wicking substance at the exterior surface of said third material in an effective amount so that said exterior surface of said third material is capable of wicking moisture, whereby said non-woven pad is formed with a first layer of intermixed fibrous material and said thermoplastic fibers having moisture-wicking substance at the exterior surface thereof which is drawn onto said conveyor upstream from said predetermined location, a second layer of intermixed fibrous material and said first material which is drawn atop said first layer at said predetermined location, and a third layer of intermixed fibrous material and said third material having moisture-wicking substance at the exterior surface thereof which is drawn atop said second layer downstream from said predetermined location.

47. A method of forming a non-woven pad of fibrous material with a first material and a thermoplastic material interspersed throughout a selected portion of the thickness thereof, comprising:
introducing fibrous material into a chamber;
applying a vacuum to draw said fibrous material onto a pad support moving in a first direction within said chamber, said fibrous material forming a non-woven pad on said pad support which increases in thickness in said first direction of movement of said pad support;
intermixing said first material with a portion of said fibrous material being drawn onto said pad support at a predetermined location within said chamber;
forming thermoplastic fibers from said thermoplastic material in a dispenser means and dispensing said thermoplastic fibers from said dispenser means into said chamber for intermixing with said fibrous material and said first material being drawn onto said pad support at said predetermined location to form a layer of intermixed fibrous material, first material and thermoplastic fibers within a predetermined portion of said thickness of said pad while maintaining another portion of said thickness of said pad substantially free of said first material and said thermoplastic fibers.

48. The method of claim 47 in which said step of applying a vacuum comprises applying a vacuum in said chamber on one side of a conveyor to draw said fibrous material onto the opposite side of said conveyor to form said non-woven pad.

49. A method of forming a non-woven pad of fibrous material with a first material and a thermoplastic material interspersed throughout a predetermined portion of the thickness thereof, comprising:
introducing fibrous material into a chamber;
applying a vacuum to draw said fibrous material onto a pad support moving in a first direction within said chamber, said fibrous material forming a non-woven pad on said pad support which increases in thickness in said first direction of movement of said pad support;
intermittently intermixing said first material with a portion of said fibrous material being drawn onto said pad support at a predetermined location within said chamber;
forming thermoplastic fibers from said thermoplastic material in a dispenser means and intermittently dispensing said thermoplastic fibers from said dispenser means into said chamber for intermixing with said fibrous material and said first material being drawn onto said pad support at said predetermined location to form a layer of intermixed fibrous material, first material and thermoplastic fibers within a predetermined portion of said thickness of said non-woven pad at spaced locations along the length of said non-woven pad while maintaining another portion of said thickness of said non-woven pad substantially free of said first material and said thermoplastic fibers.

50. The method of claim 49 in which said step of applying a vacuum comprises applying a vacuum in said chamber on one side of a conveyor to draw said fibrous material onto the opposite side of said conveyor to form said non-woven pad.

51. A method of forming a non-woven pad of fibrous material with a first material, a thermoplastic material and a third material interspersed throughout selected portions of the thickness thereof, comprising:
introducing fibrous material into a chamber;
applying a vacuum to draw said fibrous material onto a pad support moving in a first direction within said chamber, said fibrous material forming a non-woven pad on said pad support which increases in thickness in said first direction of movement of said pad support;
intermixing said first material with a portion of said fibrous material being drawn onto said pad support at a predetermined location within said chamber;
forming thermoplastic fibers from said thermoplastic material in a dispenser means and dispensing said thermoplastic fibers from said dispenser means into said chamber for intermixing with said fibrous material and said first material being drawn onto said pad support at said predetermined location;
intermixing said third material with said fibrous material, said first material and said thermoplastic fibers being drawn onto said pad support at said predetermined location to form a layer of intermixed fibrous material, first material, thermoplastic fibers and said third material within a predetermined portion of said thickness of said non-woven pad while maintaining another portion of said thickness of said non-woven pad substantially free of said first material, thermoplastic fibers and said third material.

52. The method of claim 51 in which said step of applying a vacuum comprises applying a vacuum in said chamber on one side of a conveyor to draw said fibrous material onto the opposite side of said conveyor to form said non-woven pad.

53. A method of forming a non-woven pad of fibrous material with a first material, a thermoplastic material and a third material interspersed throughout selected portions thereof, comprising:
introducing fibrous material into a chamber;
applying a vacuum to draw said fibrous material onto a pad support moving in a first direction within said chamber, said fibrous material forming a non-woven pad on said pad support which increases in thickness in said first direction of movement of said pad support;
intermixing a first material with a portion of said fibrous material being drawn onto said pad support at a predetermined location within said chamber;
forming thermoplastic fibers from said thermoplastic material in a dispenser means and dispensing said thermoplastic fibers from said dispenser means into said chamber for intermixing with said fibrous material being drawn onto said pad support at a location upstream from said predetermined location;

intermixing said third material with said fibrous material being drawn onto said pad support at a location downstream from said predetermined location, whereby said non-woven pad is formed with a first layer of intermixed fibrous material and thermoplastic fibers which is drawn onto said pad support upstream from said predetermined location, a second layer of intermixed fibrous material and first material which is drawn atop said first layer at said predetermined location, and a third layer of intermixed fibrous material and third material which is drawn atop said second layer downstream from said predetermined location.

54. The method of claim 53 in which said step of applying a vacuum comprises applying a vacuum in said chamber on one side of a conveyor to draw said fibrous material onto the opposite side of said conveyor to form said non-woven pad.

55. A method of forming a non-woven pad of fibrous material with a first material and a thermoplastic material interspersed throughout a selected portion of the thickness thereof, comprising:

introducing fibrous material into a chamber;

applying a vacuum in said chamber to draw said fibrous material onto a conveyor moving through said chamber, said fibrous material forming a non-woven pad having a bottom surface resting on one side of said conveyor and a top surface which slopes upwardly relative to said conveyor from the inlet toward the outlet of said chamber;

dispensing said first material into said chamber at a predetermined location along said upwardly sloping top surface of said non-woven pad, said first material being intermixed with a portion of said fibrous material being drawn onto said conveyor at said predetermined location;

forming thermoplastic fibers from said thermoplastic material in a dispenser means and dispensing said thermoplastic fibers from said dispenser means into said chamber so that said thermoplastic fibers intermix with said fibrous material and said first material being drawn onto said conveyor at said predetermined location to form a layer of intermixed fibrous material, first material and thermoplastic fibers within a predetermined portion of said thickness of said pad while maintaining another portion of said thickness of said pad substantially free of said first and second materials.

56. The method of claim 55 in which said step of dispensing said first material comprises dispensing highly moisture-absorbent material.

57. The method of claim 56 in which said step of forming and dispensing said thermoplastic fibers includes dispensing fibers of thermoplastic material for intermixing with said fibrous material and said highly moisture-absorbent material at said predetermined location to form a layer of intermixed fibrous material, highly moisture-absorbent material and thermoplastic fibers wherein said thermoplastic fibers substantially retain said highly moisture-absorbent material with said layer of said non-woven pad.

58. A method of forming a non-woven pad of fibrous material with a first material and a thermoplastic material interspersed throughout a predetermined portion of the thickness thereof, comprising:

introducing fibrous material into a chamber;

applying a vacuum in said chamber to draw said fibrous material onto a conveyor moving through said chamber, said fibrous material forming a non-woven pad having a bottom surface resting atop said conveyor and a top surface which slopes upwardly relative to said conveyor from the inlet toward the outlet of said chamber;

intermittently dispensing said first material into said chamber at a predetermined location along said upwardly sloping top surface of said non-woven pad, said first material being intermixed with a portion of said fibrous material being drawn onto said conveyor at said predetermined location;

forming thermoplastic fibers from said thermoplastic material in a dispenser means and intermittently dispensing said thermoplastic fibers from said dispenser means into said chamber so that said thermoplastic fibers intermix with said fibrous material and said first material being drawn onto said conveyor at said predetermined location to form a layer of intermixed fibrous material, first material and thermoplastic fibers within a predetermined portion of said thickness of said non-woven pad at spaced locations along the length of said non-woven pad while maintaining another portion of the thickness of said non-woven pad substantially free of said first and second materials.

59. The method of claim 58 in which said step of dispensing said first material comprises dispensing highly moisture-absorbent material.

60. The method of claim 59 in which said step of forming and intermittently dispensing said thermoplastic fibers comprises intermittently dispensing fibers of thermoplastic material for intermixing with said fibrous material and said highly moisture-absorbent material at said predetermined location to form a layer of intermixed fibrous material, highly moisture-absorbent material and thermoplastic fibers at predetermined locations along the length of said non-woven pad wherein said thermoplastic fibers substantially retain said highly moisture-absorbent material within said layer of said non-woven pad.

61. A method of forming a non-woven pad of fibrous material with a first material, a thermoplastic material and a third material interspersed throughout selected portions of the thickness thereof, comprising:

introducing fibrous material into a chamber;

applying a vacuum in said chamber to draw said fibrous material onto a conveyor moving through said chamber between an inlet and outlet thereof, said fibrous material forming a non-woven pad on said conveyor which increases in thickness in a direction from said inlet of said chamber toward said outlet thereof, said non-woven pad having a bottom surface resting on said conveyor and a top surface which slopes upwardly relative to said conveyor from the inlet of said chamber toward said outlet thereof;

dispensing said first material into said chamber at a predetermined location relative to said upwardly sloping top surface of said non-woven pad for intermixing with a portion of said fibrous material being drawn onto said conveyor at said predetermined location;

forming thermoplastic fibers from said thermoplastic material in a dispenser means and dispensing said thermoplastic fibers from said dispenser means into said chamber for intermixing with said fibrous material and said first material being drawn onto said pad support at said predetermined location;

dispensing a third material into said chamber at said predetermined location for intermixing with said fibrous material, said first material and said thermoplastic fibers being drawn onto said conveyor thereat to form a layer of intermixed fibrous material, first material, thermoplastic fibers and third material within a predetermined portion of the thickness of said non-woven pad while maintaining another portion of said thickness of said non-woven pad substantially free of said first material, thermoplastic fibers and third material.

62. The method of claim 61 in which said step of forming and dispensing thermoplastic fibers into said chamber includes forming and dispensing thermoplastic fibers from thermoplastic material having properties which enhance the tear strength of said non-woven pad.

63. The method of claim 61 in which said step of forming and dispensing thermoplastic fibers into said chamber includes forming and dispensing thermoplastic fibers from a thermoplastic material which maintains air spaces within said fibrous material within said intermixed layer so that said non-woven pad has the desired loft.

64. The method of claim 61 in which said step of dispensing said first material into said chamber comprises dispensing a highly moisture-absorbent material for intermixing with said fibrous material within said layer of said non-woven pad.

65. A method of forming a non-woven pad of fibrous material with a first material, a thermoplastic material and a third material interspersed throughout selected portions thereof, comprising:

introducing fibrous material into a chamber;

applying a vacuum in said chamber to draw said fibrous material onto a conveyor moving through said chamber between an inlet and outlet thereof, said fibrous material forming a non-woven pad on said conveyor which increases in thickness in a direction from said inlet of said chamber toward said outlet thereof, said non-woven pad having a bottom surface resting on said conveyor and a top surface which slopes upwardly relative to said conveyor from the inlet of said chamber toward said outlet thereof;

dispensing a first material into said chamber at a predetermined location relative to said upwardly sloping top surface of said non-woven pad for intermixing with a portion of said fibrous material being drawn onto said conveyor at said predetermined location;

forming thermoplastic fibers from said thermoplastic material in a dispenser means and dispensing said thermoplastic fibers from said dispenser means into said chamber for intermixing with said fibrous material being drawn onto said conveyor at said predetermined location;

dispensing a third material into said chamber for intermixing with said fibrous material being drawn onto said conveyor at a location downstream from said predetermined location, whereby said non-woven pad is formed with a first layer of intermixed fibrous material and thermoplastic fibers which is drawn onto said conveyor upstream from said predetermined location, a second layer of intermixed fibrous material and first material which is drawn atop said first layer of said predetermined location, and a third layer of intermixed fibrous material and third material which is drawn atop said second layer downstream from said predetermined location.

66. The method of claim 65 in which said step of dispensing said first material comprises dispensing a highly moisture-absorbent material.

67. The method of claim 65 in which said step of dispensing said third material comprises dispensing thermoplastic fibers formed from a thermoplastic material.

68. A method of forming a non-woven pad of fibrous material with a first material and a thermoplastic material interspersed throughout a selected portion of the thickness thereof, comprising:

introducing fibrous material into a chamber;

applying a vacuum in said chamber to draw said fibrous material onto a conveyor moving through said chamber, said fibrous material forming a non-woven pad having a bottom surface resting on one side of said conveyor and a top surface which slopes upwardly relative to said conveyor from the inlet toward the outlet of said chamber;

dispensing said first material into said chamber at a predetermined location along said upwardly sloping top surface of said non-woven pad, said first material being intermixed with a portion of said fibrous material being drawn onto said conveyor at said predetermined location;

forming thermoplastic fibers from said thermoplastic material in a dispenser means and dispensing said thermoplastic fibers from said dispenser means into said chamber so that said thermoplastic fibers intermix with said fibrous material and said first material being drawn onto said conveyor at said predetermined location;

dispensing a moisture-wicking substance at the exterior surface of said thermoplastic material in an effective amount so that said exterior surfaces of said thermoplastic fibers formed therefrom are capable of wicking moisture, whereby a layer of intermixed fibrous material, first material and thermoplastic fibers having moisture-wicking material at the exterior surface thereof is formed within a predetermined portion of said thickness of said pad while maintaining another portion of said thickness of said pad substantially free of said first material and said thermoplastic fibers.

69. The method of claim 68 in which said step of positioning a moisture-wicking substance comprises applying a moisture-wicking substance onto the exterior surface of said thermoplastic material.

70. The method of claim 68 in which said step of positioning a moisture-wicking substance comprises intermixing said thermoplastic material and said moisture-wicking substance to form a blend in which at least a portion of said moisture-wicking substance is located at the exterior surface of said thermoplastic material.

71. The method of claim 68 in which said step of dispensing said thermoplastic fibers formed from said thermoplastic material comprises dispensing fibers having an exterior surface, said step of positioning a moisture-wicking substance comprises applying the moisture-wicking substance onto said exterior surface of said thermoplastic fibers.

72. The method of claim 68 in which said step of positioning a moisture-wicking substance comprises intermixing said thermoplastic material with said moisture-wicking material to form a blend which is supplied to at least one die head, said blend being discharged from said die head to form said thermoplastic fibers wherein at least a portion of said moisture-wicking substance is located at the exterior surface of said thermoplastic fibers.

73. A method of forming a non-woven pad of fibrous material with a first material, a thermoplastic material and a third material interposed throughout selected portions thereof, comprising:

introducing fibrous material into a chamber;

applying a vacuum in said chamber to draw said fibrous material onto a conveyor moving through said chamber between an inlet and outlet thereof, said fibrous material forming a non-woven pad on said conveyor which increases in thickness in a direction from said inlet of said chamber toward said outlet thereof, said non-woven pad having a bottom surface resting on said conveyor and a top surface which slopes upwardly relative to said conveyor from the inlet of said chamber toward said outlet thereof;

dispensing a first material into said chamber at a predetermined location relative to said upwardly sloping top surface of said non-woven pad for intermixing with a portion of said fibrous material being drawn onto said conveyor at said predetermined location;

forming thermoplastic fibers from said thermoplastic material in a dispenser means and dispensing said thermoplastic fibers from said dispenser means into said chamber for intermixing with said fibrous material being drawn onto said conveyor at a location upstream from said predetermined location;

positioning a moisture-wicking substance at the exterior surface of said thermoplastic material in an effective amount so that the exterior surfaces of said thermoplastic fibers formed from said thermoplastic material are capable of wicking moisture;

dispensing a third material into said chamber for intermixing with said fibrous material being drawn onto said conveyor at a location downstream from said predetermined location;

positioning a moisture-wicking substance at the exterior surface of said third material in an effective amount so that said exterior surface of said third material is capable of wicking moisture, whereby said non-woven pad is formed with a first layer of intermixed fibrous material and thermoplastic fibers having moisture-wicking substance at the exterior surface thereof which is drawn onto said conveyor upstream from said predetermined location, a second layer of intermixed fibrous material and first material which is drawn atop said first layer at said predetermined location, and a third layer of intermixed fibrous material and third material having moisture-wicking substance at the exterior surface thereof which is drawn atop said second layer downstream from said predetermined location.

74. The method of claim 73 in which said step of dispensing said first material comprises dispensing a highly moisture-absorbent material.

75. The method of claim 73 in which said step of dispensing said third material comprises dispensing a thermoplastic material.

76. The method of claim 73 in which said steps of positioning a moisture-wicking substance comprise intermixing said thermoplastic material and said moisture-wicking substance to form a blend in which at least a portion of said moisture-wicking substance is located at the exterior surface of said thermoplastic material, and intermixing said third material and said moisture-wicking substance to form a blend in which at least a portion of said moisture-wicking substance is located at the exterior surface of said third material.

77. The method of claim 73 in which said steps of dispensing said thermoplastic material and said third material each comprises dispensing fibers into said forming chamber having an exterior surface, said steps of positioning a moisture-wicking substance comprising applying the moisture-wicking substance onto said exterior surface of said fibers of thermoplastic material and said third material.

78. The method of claim 73 in which said steps of positioning a moisture-wicking substance comprise:

intermixing said thermoplastic material with said moisture-wicking material to form a blend which is supplied to a first die head, said blend being discharged from said die head to form said thermoplastic fibers wherein at least a portion of said moisture-wicking substance is located at the exterior surface of said thermoplastic fibers; and intermixing said third material with said moisture-wicking material to form a blend which is supplied to a second die head, said blend being discharged from said die head to form fibers wherein at least a portion of said moisture-wicking substance is located at the exterior surface of said fibers.

* * * * *